United States Patent
Wang et al.

(10) Patent No.: US 10,433,911 B2
(45) Date of Patent: Oct. 8, 2019

(54) OPTICAL TARGETING AND VISUALIZATION OF TRAJECTORIES

(71) Applicant: iMIRGE Medical INC., London (CA)

(72) Inventors: Hao Wang, London (CA); Neil Duggal, London (CA)

( * ) Notice: Subject to any disclaimer, the term of this patent is extended or adjusted under 35 U.S.C. 154(b) by 495 days.

(21) Appl. No.: 15/006,951

(22) Filed: Jan. 26, 2016

(65) Prior Publication Data

US 2016/0166333 A1    Jun. 16, 2016

Related U.S. Application Data

(63) Continuation-in-part of application No. 14/490,610, filed on Sep. 18, 2014.

(Continued)

(51) Int. Cl.
*A61B 5/05*      (2006.01)
*A61B 34/10*    (2016.01)
(Continued)

(52) U.S. Cl.
CPC .......... *A61B 34/10* (2016.02); *A61B 5/0059* (2013.01); *A61B 17/00* (2013.01); *A61B 34/20* (2016.02);
(Continued)

(58) Field of Classification Search
CPC ....... A61B 34/10; A61B 5/0059; A61B 90/11; A61B 90/13; A61B 90/30; A61B 34/20; A61B 17/00; A61B 8/0841; A61B 6/4441; A61B 6/12; A61B 6/582; A61B 6/461; A61B 8/461; A61B 8/4416; A61B 2090/3954; A61B 90/361; A61B 2090/363; A61B 2090/364; A61B 2017/00398;
(Continued)

(56) References Cited

U.S. PATENT DOCUMENTS

| | | |
|---|---|---|
| 5,212,720 A | 5/1993 | Landi et al. |
| 5,230,623 A | 7/1993 | Guthrie et al. |

(Continued)

FOREIGN PATENT DOCUMENTS

| | | |
|---|---|---|
| CN | 102813504 | 12/2012 |
| JP | 2003260064 A | 9/2003 |
| WO | WO2015039246 | 3/2015 |

OTHER PUBLICATIONS https://www.healthcare.siemens.com/angio/options-and-upgrades/clinical-software-applications/syngo-iguide Believed to have been published on or before Aug. 12, 2014.

*Primary Examiner* — Sanjay Cattungal
(74) *Attorney, Agent, or Firm* — David Meibos; Maywood IP Law

(57) ABSTRACT

Enhanced targeting systems and methods may be used to visualize trajectories for surgical instruments. Such a targeting system may have a first light source and a second light source. The first light source may project first light along a first plane, and the second light source may project second light along a second plane nonparallel to the first plane. At an intersection of the first and second planes, the first light and the second light may cooperate to produce a targeting line that indicates the desired trajectory. An image capture system may also be used to capture image data of anatomical features of a patient at one or more locations in space, and a controller may receive the image data and indicate the trajectory relative to the anatomical features of the patient.

20 Claims, 26 Drawing Sheets

Related U.S. Application Data

(60) Provisional application No. 62/108,193, filed on Jan. 27, 2015, provisional application No. 61/879,620, filed on Sep. 18, 2013, provisional application No. 62/051,784, filed on Sep. 17, 2014.

(51) Int. Cl.

| | | |
|---|---|---|
| *A61B 17/00* | (2006.01) | |
| *A61B 90/30* | (2016.01) | |
| *A61B 34/20* | (2016.01) | |
| *A61B 90/11* | (2016.01) | |
| *A61B 90/13* | (2016.01) | |
| *A61B 5/00* | (2006.01) | |
| *A61B 90/00* | (2016.01) | |
| *A61B 8/00* | (2006.01) | |
| *A61B 6/12* | (2006.01) | |
| *A61B 6/00* | (2006.01) | |
| *A61B 8/08* | (2006.01) | |

(52) U.S. Cl.
CPC .............. *A61B 90/11* (2016.02); *A61B 90/13* (2016.02); *A61B 90/30* (2016.02); *A61B 6/12* (2013.01); *A61B 6/4441* (2013.01); *A61B 6/461* (2013.01); *A61B 6/582* (2013.01); *A61B 8/0841* (2013.01); *A61B 8/4416* (2013.01); *A61B 8/4438* (2013.01); *A61B 8/461* (2013.01); *A61B 90/361* (2016.02); *A61B 2017/00398* (2013.01); *A61B 2034/107* (2016.02); *A61B 2090/363* (2016.02); *A61B 2090/364* (2016.02); *A61B 2090/3916* (2016.02); *A61B 2090/3954* (2016.02); *A61B 2090/3966* (2016.02); *A61B 2090/3991* (2016.02)

(58) Field of Classification Search
CPC .......... A61B 8/4438; A61B 2090/3966; A61B 2034/107; A61B 2090/3991; A61B 2090/3916
USPC .......................................... 600/424; 606/130
See application file for complete search history.

(56) References Cited

U.S. PATENT DOCUMENTS

| | | |
|---|---|---|
| 5,662,111 A | 9/1997 | Cosman |
| 5,782,842 A | 7/1998 | Kloess et al. |
| 5,807,387 A | 9/1998 | Druais |
| 6,178,340 B1 | 1/2001 | Svetliza |
| 6,187,018 B1 | 2/2001 | Sanjay-Gopal et al. |
| 7,281,849 B2 | 10/2007 | Sohal et al. |
| 7,603,163 B2 | 10/2009 | McNeirney et al. |
| 8,246,352 B2 | 8/2012 | Takebayashi |
| 8,265,731 B2 | 9/2012 | Kukuk et al. |
| 8,271,069 B2 | 9/2012 | Jascob et al. |
| 8,332,012 B2 | 12/2012 | Kienzle, III |
| 8,412,308 B2 | 4/2013 | Goldback |
| 8,467,851 B2 | 6/2013 | Mire et al. |
| 8,467,852 B2 | 6/2013 | Csavoy |
| 8,473,026 B2 | 6/2013 | Ferre |
| 2004/0005061 A1* | 1/2004 | Buer .................... G06F 21/602 380/282 |
| 2009/0274271 A1* | 11/2009 | Pfister .................... A61B 6/12 378/62 |
| 2014/0100620 A1* | 4/2014 | Mullaney ........... A61B 17/1725 606/86 R |
| 2014/0107473 A1* | 4/2014 | Dumoulin .............. A61B 17/17 600/424 |
| 2014/0407473 | 4/2014 | Dumoulin et al. |
| 2014/0276000 A1* | 9/2014 | Mullaney ................ A61B 34/20 600/424 |

\* cited by examiner

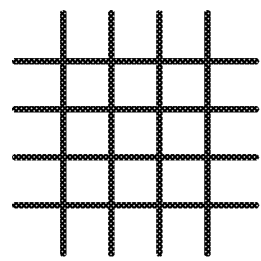
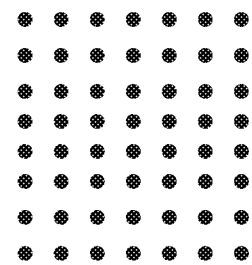
FIG. 27
FIG. 28
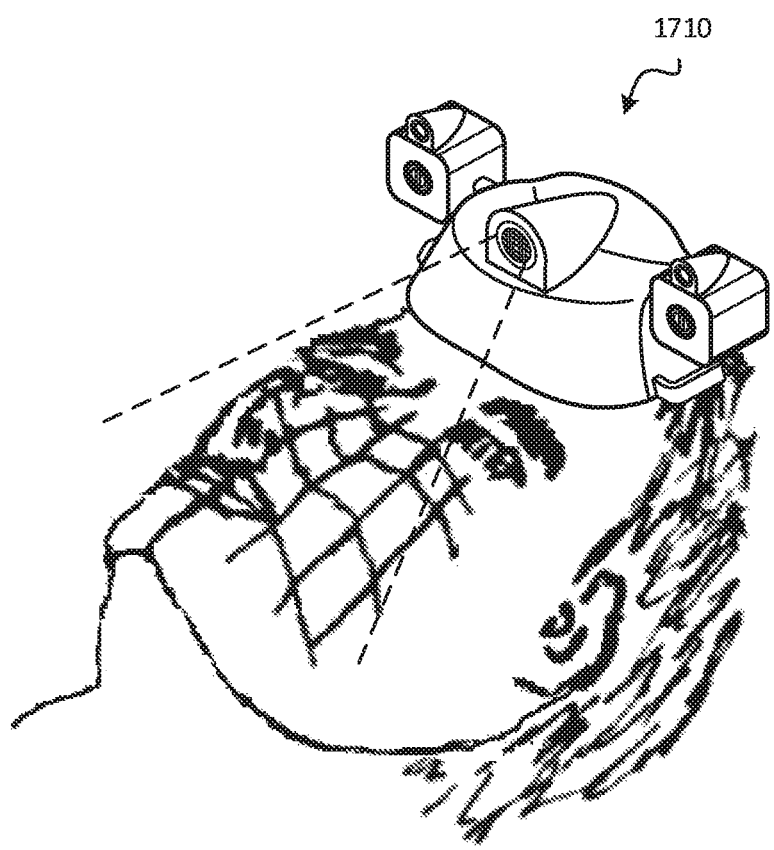
FIG. 29

OPTICAL TARGETING AND VISUALIZATION OF TRAJECTORIES

CROSS-REFERENCE TO RELATED APPLICATIONS

The present application claims the benefit of U.S. Provisional Patent Application Ser. No. 62/108,193, entitled OPTICAL TARGETING AND VISUSALIZATION OF TRAJECTORIES, which was filed on Jan. 27, 2015. The present application also claims the benefit of U.S. patent application Ser. No. 14/490,610, entitled OPTICAL TARGETING AND VISUSALIZATION OF TRAJECTORIES, which was filed on Sep. 18, 2014. U.S. patent application Ser. No. 14/490,610 claims the benefit of U.S. Provisional Patent Application Ser. No. 61/879,620, entitled OPTICAL TARGETING AND VISUALIZATION OF TRAJECTORIES, which was filed on Sep. 18, 2013. U.S. patent application Ser. No. 14/490,610 also claims the benefit of U.S. Provisional Patent Application Ser. No. 62/051,784, entitled OPTICAL TARGETING AND VISUSALIZATION OF TRAJECTORIES, which was filed on Sep. 17, 2014. All of the foregoing documents are incorporated by reference as though set forth herein in their entirety.

TECHNICAL FIELD

The present disclosure relates to medical systems and methods. More specifically, the present disclosure relates to systems and methods for aligning medical instruments with anatomical targets.

BACKGROUND

Various imaging techniques, such as X-rays, fluoroscopy, ultrasound, computed tomography (CT), and magnetic resonance imaging (MRI) play an integral role in a wide variety of medical procedures. The term "image assisted" may be used to describe medical procedures utilizing some type of imaging technique to guide the medical procedure.

The incorporation of image guidance systems into various procedures allows a physician to correlate a desired location of a patient's anatomy to images taken pre-operatively or intra-operatively using various imaging modalities such as x-rays, ultrasounds, CT scans, MRI's, etc. The use of image guidance systems also imparts the ability to look through superficial layers of anatomy to visualize deeper targets of interest. Further, image guidance systems provide the guidance needed to access target areas of interest within the patient's anatomy through the use of pre-defined entry points and/or target zones. Often, physicians rely heavily on imaging systems when a target cannot be directly visualized in order to avoid damage to surrounding anatomical structures and to minimize unnecessary tissue trauma.

There are at least two "spaces" that may be used in image guidance systems. The first may be referred to as the "image space," which may represent the imaging acquired prior to or during a procedure, such as an MRI scan of a specific anatomical area performed before surgery. From cross-sectional imaging, a three-dimensional data set may be constructed using the first image space's coordinate system, usually expressed as a Cartesian system with an arbitrary origin and principle axis. The second space may be the actual physical space surrounding the patient. This is often restricted to a specific anatomical part, such as the head, lower back, hip joint, etc., in order to improve local resolution and system performance. An image guidance system may include a mechanism for accurately measuring position within the patient's physical space, much like a tracking device. The tracking device may have its own coordinate system which may be different from that of the "image space." In order to provide flexibility, a "reference" may be held in a rigid relationship relative to the patient's anatomical area of interest. The reference can serve as an arbitrary origin of the patient's physical space and all three-dimensional spatial measurements of the patient's physical space can be expressed relative to the reference. The use of a reference can allow for the movement of the image guidance system and/or the movement of the target anatomical region of the patient without losing registration or affecting guidance accuracy. Thus, the tracking device or reference may be used for spatial recognition to read the coordinates of any point in three-dimensional space and allow accurate tracking of the physical space around the patient. An image guidance system also may include various probes to allow tracking of instruments (e.g., surgical instruments, endoscopic tools, biopsy needles, etc.) during operation to provide flexibility with regards to navigational options. The probe may also act as the tracking device or reference.

After the two coordinate systems have been established, the image space may be correlated to the physical space through a process known as registration. Registration refers to the coordinate transformation of one space into another. This is usually a linear and rigid transformation in which only translation and rotation takes place and scaling or local deformation transformations are not necessary.

Once registration is completed, a probe or other device may be used to touch various anatomical structures on the subject (physical space), and the corresponding images of the same anatomical structures may be displayed (image space). The image guidance system may also include multi-planar reconstruction capabilities that can display three-dimensional image datasets in any arbitrary plane allowing users to view surrounding structures in any arbitrary direction.

An image guidance system may include an information processing unit (e.g., a computer). The information processing unit can load a patient's pre-operative and/or intra-operative images and run software that performs registration of a patient's image space to the patient's physical space and provide navigational information to the operator (e.g., surgeon). The software may also include the ability to perform multi-planar reconstructions and targeting/trajectory planning to identify specific entry points, trajectories, target zones, etc. More advanced functions may include image fusion capabilities across imaging modalities such as fusing CT imaging data with MRI imaging data, as well as advanced image segmentation to provide surgeons with live intraoperative guidance. For example, advanced image segmentation may include extracting image information of a patients inner anatomy, (e.g., a tumor, blood vessels, tissues, etc.), rendering three-dimensional models of these structures, and then visually overlaying these structures on a display screen in a manner that shows the relative depth of the tissues/structures inside the patient (e.g., the depth of the tissues/structures relative to the patient's surface anatomy, skin, other tissues/structures, etc.). In this manner, a virtual three-dimensional view of the patient's inner and outer anatomy may be presented to the operator to help the operator visualize the inner locations and depth of tissues/structures inside the patient relative to the patient's surface anatomy.

There are many different ways of implementing an image guidance system. For example, an optical system may include a stereo camera (i.e., two cameras mounted a known fixed distance apart) that cooperate to provide accurate three-dimensional localization. The method of tracking in this example can be passive or active. In passive tracking, the system can emit infrared radiation (usually through a ring of infrared light emitting diodes, or LED's, mounted around each camera) and passive optical markers can reflect the radiation back to the cameras to allow the markers to be seen by the cameras. The markers can be small spheres of a pre-defined diameter coated in a reflective coating that may be optimized for the wavelength of infrared radiation. In active tracking, the markers themselves may be infrared LED's that emit infrared radiation that can be directly seen by the camera. Three or more markers may be arranged in a predefined geometry to give total specification of a unique vector with 6 degrees of freedom (DOF), three degrees of freedom in translation and three degrees of freedom in rotation. By altering the predefined geometry of the markers, the system can recognize and simultaneously track various probes and tools, including the special "reference probe" that defines the arbitrary origin in the physical space. Optical systems may also include software that performs image registration and navigational information to the end user.

Other example image guidance systems may employ magnetic field generators to generate a uniform gradient field to track spatial localizations. In these systems, a magnetic sensor may be used to measure the strength and direction of the magnetic field, and based on this information, spatial localization may be derived. Similarly, in these systems a reference point may be fixed to the patient and/or various probes may also be available for flexible navigation.

Another example image guidance system may be a stereotactic system. For cranial procedures, these systems may rely upon the attachment of a rigid frame around a patient's head. Cross-sectional imaging (e.g., CT, MRI, etc.) may be taken of the patient's head with the frame rigidly attached to patient's head. The frame may provide measurement of the physical space around the patient's head that directly correlates with the image space since the frame is simultaneously captured on the cross-sectional imaging scan. Thus, registration of the image space and physical space occurs automatically once a common arbitrary coordinate system is chosen on the scan.

Currently, guidance of surgical tools in these systems may be achieved mechanically (e.g., an external mechanism may direct the surgeon's instrument down a machined groove or bore). However, the surgeon must rely solely on trajectory calculations since no visual feedback is available in the absence of real-time imaging (e.g., intra-operative CT scanning, MRI scanning, etc.). Mechanical guidance can be expressed in various coordinate systems—Cartesian, polar, spherical, or mixed. Mechanical guides may rely on the "arc" principle, whereby the arc is always centered over the target. This may allow the surgeon to pick any ring or arc angle to find the most optimal placement of an entry site. Alternatively, an entry site may be predefined and arc/ring angles may be calculated. Various size guides may be available to accommodate various instrument diameters. However, since current systems cannot provide live image guidance, their roles may be limited to simple procedures, such as biopsies, placement of electrodes, etc.

Image navigation has proven to be extremely useful in improving accuracy of targeting, avoiding damage to surrounding critical structures, and improving patient outcomes. However, accurate targeting of deep anatomical structures is challenging across multiple disciplines. There is a need for an image guidance systems that facilitate identification of ideal trajectories that are difficult to visualize.

There are several clinical applications that may benefit from such improved targeting methods. One example is the insertion of external ventricular drains (EVD) or ventricular shunts (ventricular peritoneal, ventricular atrial, ventricular pleural, etc.). EVD procedures may be performed to release/redirect cerebrospinal fluid (CSF) and/or monitor intracranial pressure (ICP). The current standard of care in EVD procedures involves a blind passage of the ventricular catheter from the skin surface to the deep ventricular system in the brain via crude external landmarks. Current image guided systems used in this procedure rely upon rigid fixation of the head and access to the operating room. In addition, the use of existing image guided systems may significantly lengthen the procedure time, making their use in the emergency setting unsuitable, especially when urgent control of ICP is needed.

Another clinical application that may benefit from improved targeting methods is the performance of biopsies and related procedures. Accurate targeting of soft tissue, bone, fluid, or anatomical spaces may be used to facilitate biopsy, device placement, and/or pharmacological agent delivery. For example, a common cranial application is a stereotactic biopsy. Traditional methods have focused on frame-based stereotactic biopsy that relies upon the application of a frame secured to the skull with sharp pins that penetrate the outer table of the skull. This procedure is painful for the patient and cumbersome to set up. Recent advancements in image guidance systems have allowed the development of "frameless stereotaxy." In this instance, the pre-procedural application of a frame followed by imaging of the patient with his/her head in the frame may be avoided. However, the head still needs to be rigidly fixed with penetrating pins in a skull clamp. With these systems, patients are typically given a general anesthetic because of the pain associated with fixating the skull and the immobilization that the patient experiences. Furthermore, in frameless stereotaxy systems the targeting information is shifted entirely to the guidance system and the screen requiring the surgeon to periodically look away from his or her hands and surgical instruments to view the screen for trajectory guidance.

Similar systems have been deployed to place electrodes or other implants. For instance, deep brain stimulator or RF ablation electrode insertion into cranial structures employs similar steps as a stereotactic biopsy. In this instance, the goal is to place an implant into a pre-defined area of the brain. Again, utilizing similar image-guided techniques, abnormal fluid or soft tissue collections including, but not limited to intracerebral abscesses, hematomas, or protein collections can be targeted.

There are numerous potential applications of the image-guided techniques disclosed herein for orthopedic procedures, ranging from placement of implants to placement of nails, plates, screws, and the like. For example, in hip replacement surgeries, accurate placement of the acetabular cap with specific angles of abduction/adduction and flexion/extension has been shown to be an important factor in preventing premature wear and recurrent hip dislocations. Similarly, knee, shoulder, ankle and small joint replacements rely upon precise cuts in the adjacent bones to ensure anatomical alignment of the implant. Another example includes the placement of pedicle screws in spinal surgery, which rely upon a precise trajectory and angle of insertion to prevent neurological injury and screw misplacement. An additional frequent orthopedic application involves the placement of intramedullary nails in long bone fractures. Intramedullary nails may conform to the shape of the intramedullary canal, sometimes making accurate targeting and alignment of distal locking screw holes difficult. Unfortunately, although many attempts have been made, no satisfactory system currently exists that can easily address this problem without significantly lengthening the operative time.

Unfortunately, all of these image-guided surgical techniques currently involve access to an image guidance system, a fixation method, and an operating room. Access to such facilities and instruments may not be feasible for emergency procedures, where the delay in bringing the patient to the operating room and setting up existing image guidance systems would result in a catastrophic outcome for the patient. In these instances, the physician is often forced to resort to crude external anatomical landmarks for rough guidance. This trade-off between speed and accuracy means that patients who require emergency procedures are often not able to receive the benefits of precise image-guidance. Further, existing image guidance systems are, in many instances, expensive and cost-prohibitive for smaller medical facilities. This means that image guidance technology is typically restricted to large, well-funded hospitals. Thus, many hospitals and healthcare facilities are not equipped with traditional image guidance systems, depriving patients of the benefits of the accuracy and precision of image-guided procedures. This is particularly true in developing countries where cost is a major barrier to the adoption of image guidance technology.

Additionally, routine radiology procedures such as biopsies are performed under the guidance of plain films, CT scans, ultrasound imaging, and magnetic resonance imaging. These procedures are performed frequently and may expose radiologists and technicians to harmful doses of radiation over time. Furthermore, all of these imaging modalities require practitioners to view an image on a screen, computer terminal, or the like, instead of watching the procedure in the physical space of the patient. Thus, when using existing image guidance systems, practitioners must take their eyes off the patient and focus on the information displayed on the screen (i.e., "eyes off target"). For these critical moments, the practitioners do not have direct visual confirmation of their instrument(s). Instead they must rely on feel, muscle memory, and/or rapidly looking back and forth between the screen and the patient. Therefore, a need exists for an image guidance system that can use previous imaging studies to guide the physician as they target a structure hidden below the surface of the skin, without the use of frames or pins, while providing direct visualization within the working area of the targeting trajectory to help practitioners keep their "eyes on the target" as they visualize/target structures inside the patient.

SUMMARY

The various systems and methods of the present disclosure have been developed in response to the present state of the art, and in particular, in response to the problems and needs in the art that have not yet been fully solved by currently available visualization systems. The systems and methods of the present disclosure may provide enhanced visualization systems that facilitate a variety of medical procedures.

To achieve the foregoing, and in accordance with the disclosure as embodied and broadly described herein, the present disclosure provides enhanced systems with associated methods to visualize desired trajectories. In one example of the disclosed technology, a targeting system incorporates two or more light sources at angles nonparallel to each other to facilitate the visualization of linear trajectories. Each light source may be a laser that projects light within a plane. The lasers can be tuned to the same frequency in the visible electromagnetic spectrum to produce the same colored light. In another embodiment, the lasers are tuned to different frequencies to produce different-colored light.

Each of the lasers may project a well-defined planar field of electromagnetic radiation along its principle axis. The principle axes of the lasers may be non-parallel to each other and non-coaxial with each other such that the light from the two or more lasers intersects to produce a targeting line in three-dimensional space. Adjustment of the orientation of the plane within which light is projected may be accomplished by adjusting the orientation (for example, roll, pitch, and/or yaw) of the corresponding light source. Adjustment of the orientation of either plane may result in repositioning of the targeting line. The targeting line may be coaxial with the trajectory for which visualization is desired. The targeting line may be visualized, for example, by projecting it on an instrument. Orientation of the instrument such that the targeting line is visible as a line on the instrument may indicate that the instrument is properly oriented along the trajectory.

The system may operate with either cross-sectional imaging or planar (projection) imaging modalities. One example of cross-sectional imaging involves trajectory planning performed using either source images or multi-planar reconstruction. One or more reference markers may be applied to the patient prior to image acquisition, and the reference marker(s) may be identified during trajectory planning. In an alternative embodiment, the system may include an image-capture device, such as one or more CCD cameras that may be used in conjunction with the movable light sources mentioned previously, other light sources, and/or ambient light to capture 3-D surface information of the patient. The planned trajectory may be plotted and used, in combination with reference marker location(s) and/or 3-D surface information, to determine the orientations of the light sources that are required to project the targeting line at the proper trajectory. These orientations may be conveyed to the targeting system and used to set the orientations of the light sources. The targeting system may then be activated to project the targeting line, thereby indicating the trajectory proximate the entry point at which the instrument is to enter the patient's anatomy.

One example of a planar imaging and targeting system includes attaching the targeting system directly to a medical imaging device (for example, the image intensifier of a fluoroscopy unit). With the medical imaging device, two images may be taken orthogonal to each other of the anatomical region of interest, with rotation being the only allowed motion for the imaging device between capture of the two images. The planned trajectory may be plotted using the two orthogonal image projections. The medical imaging device may be rotated to a predefined angle prior to calculation of the orientations of the light sources. The predefined angle may be established by the user to keep the medical imaging device from impeding the procedure, while enabling the targeting system to provide the necessary trajectory visualization. Then, the trajectory may be used to generate the appropriate orientations for the light sources, which may be conveyed to the targeting system and used to set the orientations of the light sources. The targeting system may then be activated to project the targeting line. The visualized trajectory may optionally be coaxial with the central axis of the medical imaging device.

In some embodiments, additional light sources (for example, a targeting system incorporating three or more lasers) can be used to provide depth information, allow visualization of two or more trajectories simultaneously, and/or provide flexibility in the orientation of the targeting system. Thus, if the space between one or more light sources and the trajectory to be visualized is occluded by an object or person, two of the remaining light sources that are not occluded by the object or person may instead be used to project the targeting line.

In some embodiments, the addition of camera systems can be used to increase versatility of the targeting system. For example, in cross-sectional imaging modalities, the use of fiducial markers can be omitted by using the camera and/or laser systems for 3-D image acquisition of surface anatomy followed by image registration via a control unit. Furthermore, the addition of an optical tracker/reference/fiducial during or after registration allows patient anatomy to move independently of the targeting system while allowing the patient anatomy to be tracked and the registration to be continually updated. The same concept can be applied to probes or markers that allow not only trajectory visualization and targeting, but also tracking and input/feedback to the control unit. In the case of planer X-ray imaging, the use of a camera system with or without a gyroscope system may facilitate tracking of X-ray tube position and position-lock acquired X-ray images. This may allow non-isocentric and even non-orthogonal images to be used for the calculation of trajectory information, thereby expanding the versatility of planar X-ray for the use of image guidance/targeting with the disclosed technology.

The disclosed technology is versatile and has a wide range of applications, including but not limited to: targeting anatomical structures for procedures such as biopsies, ablation, injections, electrical stimulation, and the like; guiding and/or aligning placement of implants such as joint replacements, screws, rods, and the like; directing the angle of osteotomies, and guiding the placement of other instruments such as catheters, ultrasound probe, rigid endoscopes, etc. The disclosed technology may also be used to enhance the performance of current image guidance systems as well as robot-assisted procedures. Additionally, the disclosed technology may be used to perform dental applications such as alignment and/or placement of implant posts, definition of root canal trajectories, location of dental fractures, etc. Furthermore, the disclosed technology may be used in a variety of industrial applications to improve the alignment of manual procedures such as drilling, welding, finishing procedures, etc.

These and other features and advantages of the present disclosure will become more fully apparent from the following description and appended claims, or may be learned by the practice of the disclosure as set forth hereinafter.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the disclosure's scope, the exemplary embodiments of the disclosure will be described with additional specificity and detail through use of the accompanying drawings in which:

FIG. 27 illustrates an example of structured light pattern—a grid with predefined spacing and orientation;

FIG. 28 illustrates an alternative example structured light pattern—a dot matrix with predefined spacing and orientation;

FIG. 29 illustrates a targeting system with embodiments of camera system and structured light source attached to part of a patient's anatomy;

DETAILED DESCRIPTION

Exemplary embodiments of the present disclosure will be best understood by reference to the drawings, wherein like parts are designated by like numerals throughout. It will be readily understood that components of the embodiments, as generally described and illustrated in the figures herein, could be arranged and designed in a wide variety of different configurations. Thus, the following more detailed description of the embodiments of the apparatus, system, and method, as represented in FIGS. 1 through 34, is not intended to limit the scope of the present disclosure, as claimed, but is merely representative exemplary of exemplary embodiments of the present disclosure.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Figure 1:
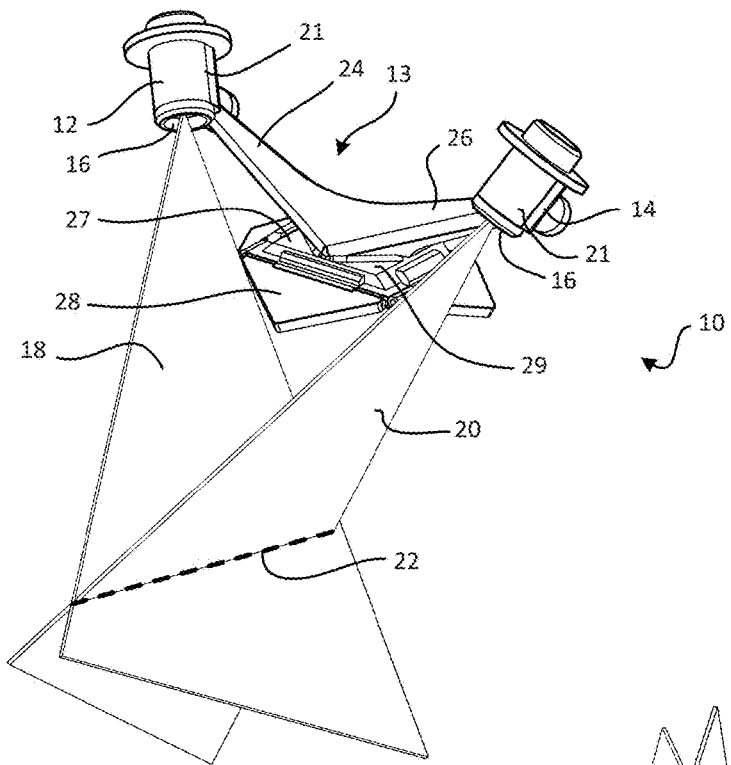
FIG. 1 is a perspective view illustrating a targeting system including a baseplate, according to one embodiment of the present disclosure.

Referring to FIG. 1, a perspective view illustrates a targeting system, or system 10, according to one exemplary embodiment. The system 10 may also be referred to as an image guided laser targeting system, a targeting system, a laser guide, and/or a guided targeting system. As embodied in FIG. 1, the system 10 may be designed to be registered directly on a patient, as will be described subsequently. The system 10 may be well-adapted for cranial procedures such as the installation of external ventricular drains (EVD's) or the like, and may be used to project a targeting line along the trajectory a surgical instrument is to follow in order to properly perform the procedure.

As illustrated in FIG. 1, the system 10 includes a first light source in the form of a first laser 12 and a second light source in the form of a second laser 14. In various embodiments, a wide variety of light sources may be used, including but not limited to lasers, light-emitting diodes (LED's), incandescent lights, fluorescent lights, and the like. Coherent light sources and/or incoherent light sources may also be used. Lasers may advantageously emit coherent light that can provide distinct and easily visible luminance, but in other embodiments, other types of light sources may be used.

The first laser 12 and the second laser 14 may each be designed to emit light along a plane. This may be accomplished, for example, by covering the emitting end of the laser with a slotted cover that permits light to exit via the slot and/or by aligning the laser light source with an optical lens that provides planar light output. Thus, the first laser 12 may emit first light along a first plane, and the second laser 14 may emit second light along a second plane, which may be nonparallel to the first plane.

The first laser 12 and the second laser 14 may be attached to a fixture that keeps the first laser 12 and the second laser 14 in fixed locations relative to each other and to the patient. In the system 10 of FIG. 1, the fixture may take the form of a base component 13 to which the first laser 12 and the second laser 14 are attached at a fixed relative distance from one another. The base component may be designed to register directly on an anatomical feature of the patient, such as the cranium.

In the system 10, the distance between the first laser 12 and the second laser 14 may be fixed. However, in alternative embodiments, the light sources can be movable relative to each other. The positions of the light sources may be accurately measured for use in calculations to accurately project a targeting line along a desired trajectory for visualization. The distance between the first laser 12 and the second laser 14 may be optimized based on the proximity of the desired instrument trajectory to the system 10. In at least one embodiment, the accuracy of the trajectory visualization may be improved by positioning the first laser 12 and the second laser 14 coplanar with a midpoint of the trajectory in an approximately equilateral triangular arrangement.

For example, in a neurosurgical setting, the base component 13 of the system 10 may be attached to a patient's forehead with the targeting area covering the convexity of the cranium. This arrangement may provide an accurate targeting range of approximately 10 cm for the insertion of an EVD, a dimension which may correspond to the distance between the first laser 12 and the second laser 14.

The first laser 12 and the second laser 14 may each include a lens 16 that is at least partially encapsulated by a casing 21. The lens 16 and/or the casing 21 may be cylindrical. The lens 16 may allow for the generation of first light 18 that originates from the first laser 12 and second light 20 that originates from the second laser 14. As shown, the first light 18 may be emitted along a first plane, and the second light may be emitted along a second plane nonparallel to the first plane.

The first laser 12 and the second laser 14 may be designed such that the first light 18 and the second light 20 are both predominantly composed of frequencies within the visible portion of the electromagnetic spectrum. The second light 20 may have a frequency different from that of the first light 18, and may thus have a color different from that of the first light 18. For example, the first light 18 may be red and the second light 20 may be green. In the rest of this specification, references to red and green lasers are to be interpreted as the first and second lasers, respectively, and are not an indication that red and green lasers are the only colors contemplated by the present disclosure. In other examples, the second laser 14 may be movably mounted relative to the first laser 12 so that the position of the second laser 14 may be adjusted relative to that of the first laser 12. The lens 16 of the first laser 12 and/or the second laser 14 may be a Gaussian lens. Additionally or alternatively, the system 10 may include one or more additional lasers, which may have various lens types, emission frequencies, and/or other parameters.

The first light 18 and the second light 20 may each originate from a laser source within the corresponding one of the first laser 12 and the second laser 14. These laser sources may be, for example, a red laser diode (not shown) in the first laser 12 and a green laser diode (not shown) in the second laser 14. Laser diodes may provide compact size and favorable energy consumption, although other laser sources may be substituted for laser diodes. The red laser diode may emit electromagnetic radiation of approximately 650 nm. The green laser diode may emit electromagnetic radiation of approximately 530 nm. The first laser 12 and the second laser 14 may be positioned such that when the first light 18 and the second light 20 are emitted, they intersect to produce a targeting line 22, which in this example may be perceived by the human eye as a yellow color due to the additive property of light. The additive color produced by adding the colors of the first laser 12 and the second laser 14 may add an additional element of distinctive visualization of the target trajectory. The additive color can vary depending on the colors of light emitted by the first laser 12 and the second laser 14. In other embodiments, one or more lasers that emit light of different wavelengths (for example, a laser that emits blue light with a wavelength of 450 nm) may be used in place of or in addition to the first laser 12 and/or the second laser 14.

The first laser 12 and the second laser 14 may be attached to the base component 13 in such a way that each has at least two degrees of rotational freedom about axes of rotation that are orthogonal to each other. For example, the first laser 12 and the second laser 14 may each be rotatable such that a relative geometrical relationship between the first laser 12 and the second laser 14 exists so that a third axis orthogonal to the first and second rotational axes remains fixed in rotation. The movement of the first laser 12 and the second laser 14 may be in the "yaw" and "roll" directions while having a fixed "pitch." In other embodiments, the first laser 12 and the second laser 14 may be fixed in rotation about the yaw direction or the roll direction, while rotation is possible about the other two directions. A translational degree of freedom may additionally or alternatively be incorporated if the distance between the lasers is adjustable.

To accurately calculate the "roll" and "yaw" of the first laser 12 and the second laser 14, the trajectory is transformed into the local coordinate system of each of the first laser 12 and the second laser 14 with the laser's center of rotation occupying the origin. The distance between the lasers is known. A plane originating from the center of the first laser 12 (the red laser) and coincident with the trajectory may be the ideal path of the first light 18. The angle of the corresponding first plane with respect to the origin may be used to calculate the roll and yaw angles. The same procedure may be carried out for the second laser 14 (the green laser). Two planes coincident with the same line may intersect at that line (since two planes in 3-D space intersect to form a unique line). As such, the two unique sets of roll and yaw angles are sufficient to determine a unique targeting line that defines a trajectory in three-dimensional space based on the intersection of the first light 18 emitted by the first laser 12 with the second light 20 emitted by the second laser 14.

Figure 2:
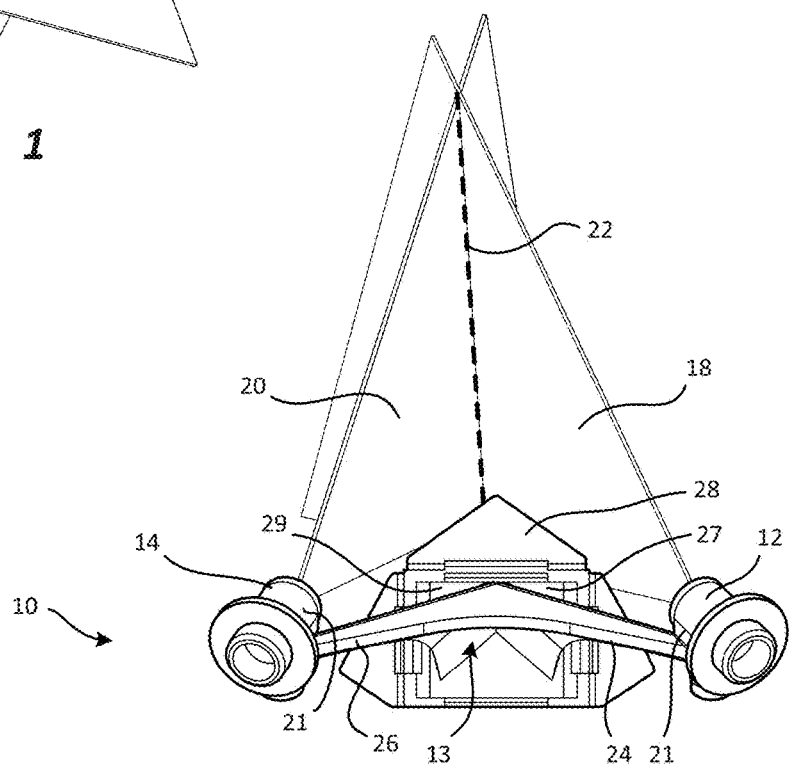
FIG. 2 is an alternative perspective view of the targeting system of FIG. 1.

Referring to FIG. 2, an alternative perspective view illustrates the system 10 of FIG. 1 with the base component 13 more easily visualized. As shown, the base component 13 may have a first arm 24, a second arm 26, a base platform 27, and a baseplate 28. The first laser 12 may be attached to the first arm 24 of the base component 13, and the second laser 14 may be attached to the second arm 26 of the base component 13. The first arm 24 and the second arm 26 may intersect at or near a top surface 29 of the base platform 27. The base platform 27 may be attachable to the baseplate 28, which may be secured to a desired anatomical feature during use.

As embodied in FIG. 2, the baseplate 28 may be a general component that serves two main purposes. First, the baseplate 28 may provide a reference to allow accurate image registration. Second, the baseplate 28 may provide an interface to attach the system 10 to the patient. In alternative embodiments, baseplates may perform one or both of these functions with a configuration different from that illustrated in FIG. 2. Alterations or permutations in baseplate features may be made to adapt the system 10 to particular local anatomy or features, depending on the specific application the system 10 is to be used for.

The baseplate 28 may include a bottom surface (not shown in FIG. 2) opposite the top surface 29 that is shaped to interface with a top portion 31 (FIG. 3A) of the baseplate 28. The base platform 27 may include grooves, holes, channels, posts and/or other features that are shaped to engage complementary features on the top portion 31 of the baseplate 28 to secure the base platform 27 to the baseplate 28. The baseplate 28 may include a bottom portion 33 (FIG. 3B) opposite the top portion 31 that is shaped to interface with the desired anatomical part or feature for which trajectory visualization is performed. The bottom portion 33 may include an adhesive material or connection features, such as pins, screws, hook and loop fastener, or other protruding and/or recessed features that allow the system 10 to be substantially secured to the appropriate anatomical feature during the procedure.

Figure 3A:
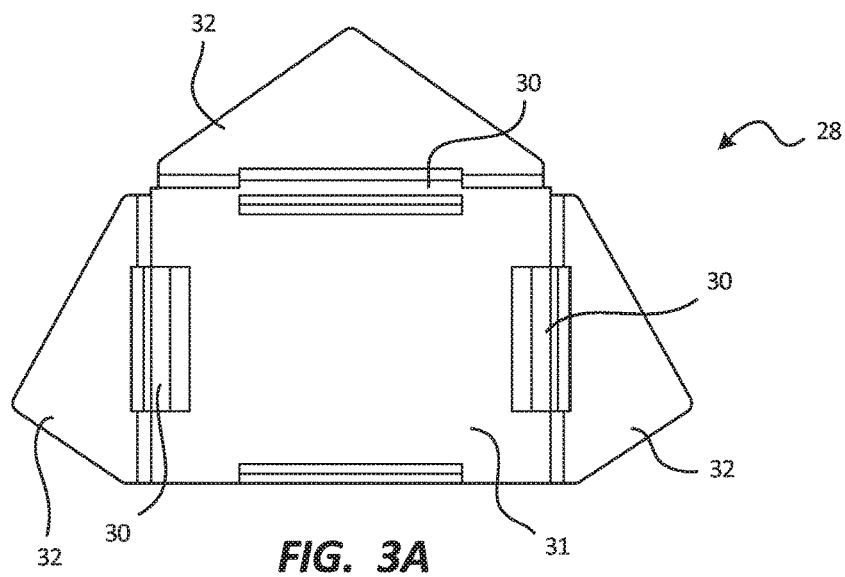
FIGS. 3A-3C are plan, front elevation, and perspective views, respectively, of the baseplate of the targeting system of FIG. 1.
Figure 3B:
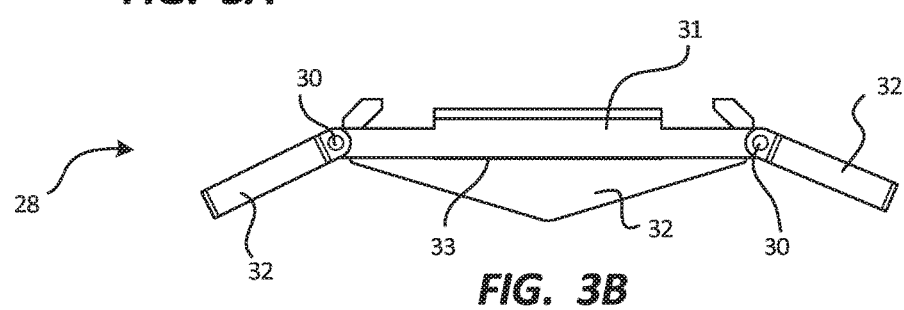
Figure 3C:
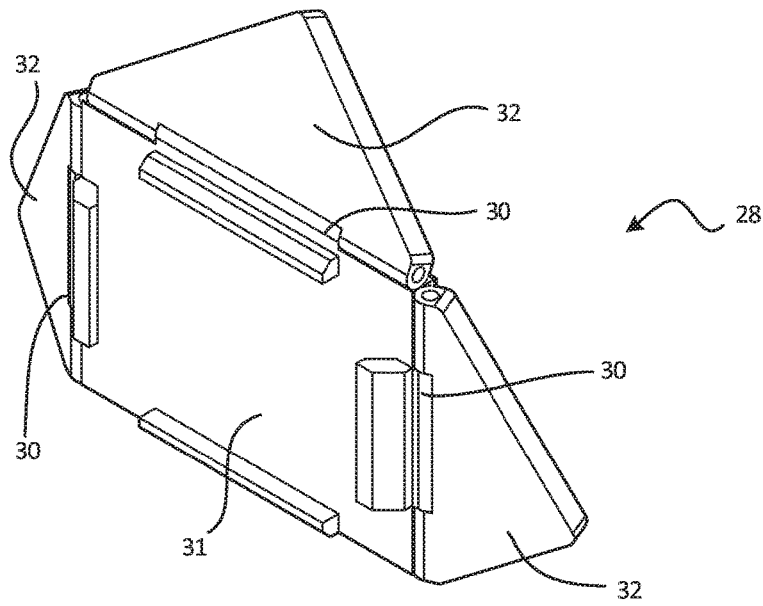

Referring to FIGS. 3A-3C, plan, front elevation, and perspective views, respectively, illustrate the baseplate 28 of the system 10 of FIG. 1. As shown, the baseplate 28 may be substantially flat, and may include one or more hinges 30, each of which may define an outside edge portion 32 in the shape of a fin. In alternative examples, the baseplate 28 may be curved or angled, in addition to or in place of the presence of hinges. Each hinge 30 may allow the corresponding one of the outside edge portions 32 to rotate about the hinge 30 to enable the baseplate 28 to conform to a complex surface topography. In the example illustrated in FIGS. 3A-3C, the baseplate 28 may include three hinges 30 such that three outside edge portions 32 may rotate about each associated hinge 30.

Figure 4A:
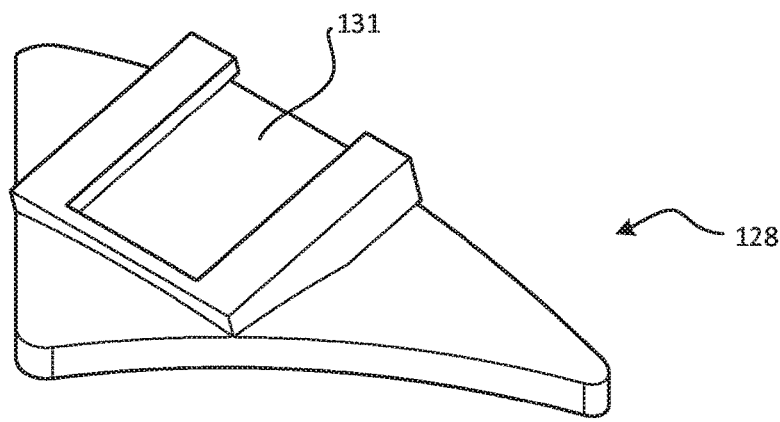
FIGS. 4A-4C are perspective, front elevation, and plan views, respectively, of a baseplate of a targeting system, according to one alternative embodiment of the present disclosure.
Figure 4B:
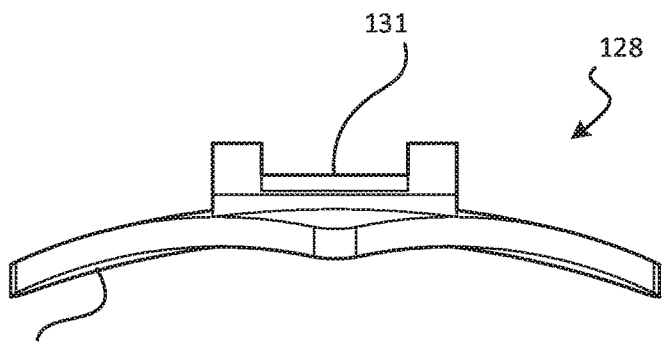
Figure 4C:
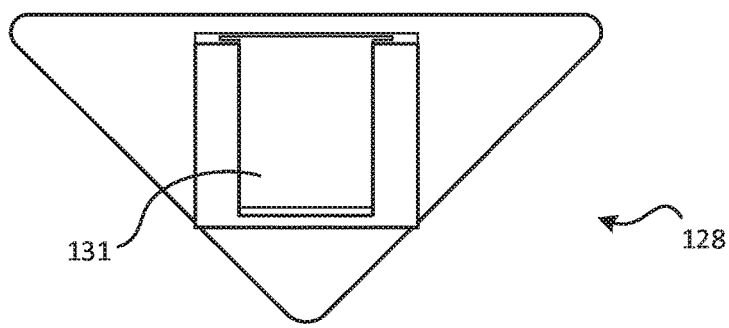

Referring to FIGS. 4A-4C, perspective, front elevation, and plan views, respectively, illustrate a baseplate 128 of a targeting system according to one alternative embodiment, with a predefined curvature and hinges or no movable fins. The baseplate 128 may have a bottom portion 133, which may have a predefined curvature to conform to a contoured anatomical surface. As shown in FIGS. 4A-4C, this curvature may be concave so that the baseplate 128 can conform to a convex surface such as a cranial surface. The baseplate 128 may also have a top portion 131 with a receptacle that mates with a corresponding feature (not shown) coupled to the first and second light sources (not shown).

Figure 5A:
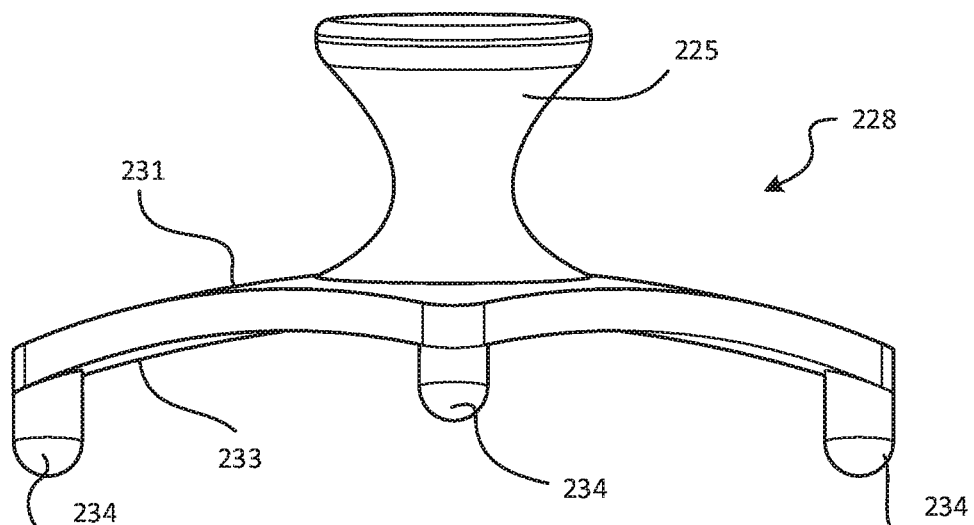
FIGS. 5A-5B are front elevation and perspective views, respectively, of a template for attaching a plurality of points or markers to a patient.
Figure 5B:
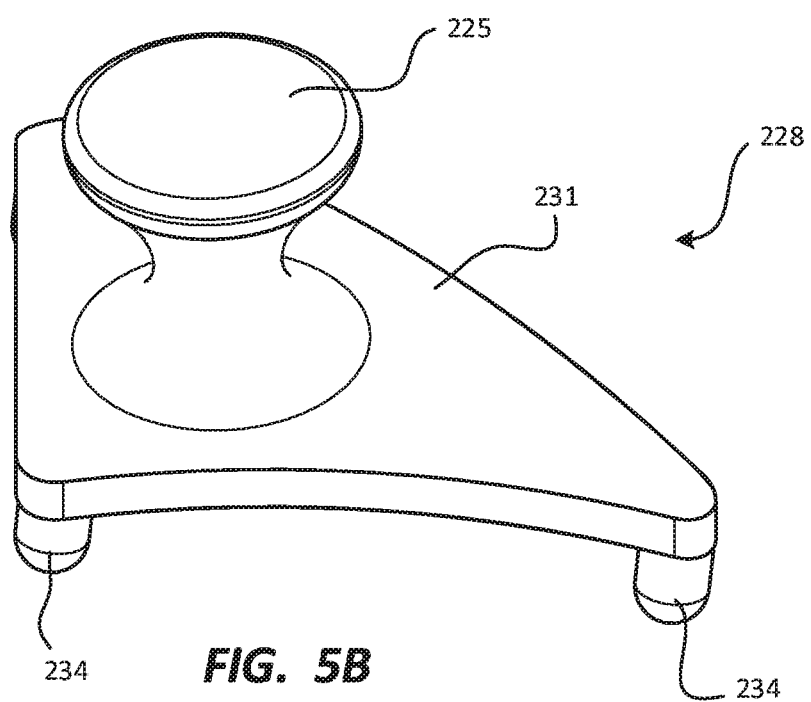

Referring to FIGS. 5A-5B, front elevation and perspective views, respectively, illustrate a template for attaching a plurality of points or markers to the patient to serve as a reference for attachment of a targeting system, such as that of FIG. 1, to the patient. As illustrated in FIGS. 5A-5B, the template may include a baseplate 228 with plurality of posts 234 that protrude from the bottom portion 233. These posts 234 may be designed to engage registration markers or fiducials which are commonly used by various image guidance systems. Such fiducials may be held in place on the anatomical feature to which the targeting system (such as the system 10 of FIG. 1) is to be attached by the posts 234. Additionally, the baseplate 228 may include a handle 225 extending form the top portion 231 of the baseplate 228. In some cases, the posts 234 themselves may act as registration markers. In operation, the fiducials (or the posts 234) may be visualized using imaging modalities such as CT scanning or MRI scanning. The posts 234 may be attached to or embedded within the baseplate 228 with a predefined geometry, and may be used in operation to calculate a reference point through the process of registration.

In the event that fiducial markers different from the posts 234 are used, the fiducial markers may be placed onto tissue in a pre-defined geometry using a baseplate 228. These fiducial markers may be incorporated into the baseplate 228 and may thus include elements such as radio-opaque materials, MRI contrast enhancing materials (e.g. copper sulfate), and the like. These fiducial markers may also be external to the baseplate 228 and/or connected to the baseplate 228. The fiducial markers may be attached to soft tissue such as skin via an adhesive backing or the like, or they may be secured directly to bone via screws and/or other fasteners. In general, attachment of the baseplate 228 to the patient may involve any combination of methods to form a solid connection. This includes but is not limited to, adhesives, hook and loop fasteners such as Velcro™, and other fasteners including but not limited to clamps, spring-loaded grips, screws, and pins. The manner in which attachment is accomplished may depend on the surgical application, the anatomical location, the type of visualization needed, and the surface properties at the anatomical location (e.g. soft tissue thickness, bone quality, and the like).

In one example of a method of use of a system 10 as in FIGS. 1-3C, and a template 228 as in FIGS. 5A-5B, an operator may place fiducial markers at an anatomical region of interest. If attached to the skin, the fiducial markers may be attached to areas of the body with bony prominence and/or minimal soft tissue in order to minimize distortion and shift. Cross-sectional imaging such as CT scanning or MRI scanning may then be performed to visualize these unique markers and generate a reference coordinate system. For example, for cranial navigation, a location with minimal soft tissue may advantageously minimize skin shift. Thus, the fiducial markers may be attached to the forehead in this example. For orthopedic applications, the iliac crest and the anterior tibia are examples of anatomical locations with minimal soft tissue coverage.

After imaging has been carried out, the desired trajectory may be established by utilizing to the image(s) that were obtained. This trajectory may be used, through the use of known geometrical transformations, to determine the required orientations of the first laser 12 and the second laser 14. The first laser 12 and the second laser 14 may be oriented at the necessary orientations and activated to project the first light 18 and the second light 20 to create and project the targeting line 22. The targeting line 22 may advantageously be projected on a surgical instrument or a visualization aid, as will be shown and described in greater detail subsequently.

The orientations of the first laser 12 and the second laser 14 may be configured automatically and/or manually. If desired, a targeting system may include a mechanism by which the user may read and/or adjust the orientations of the first laser 12 and the second laser 14 manually.

Figure 6A:
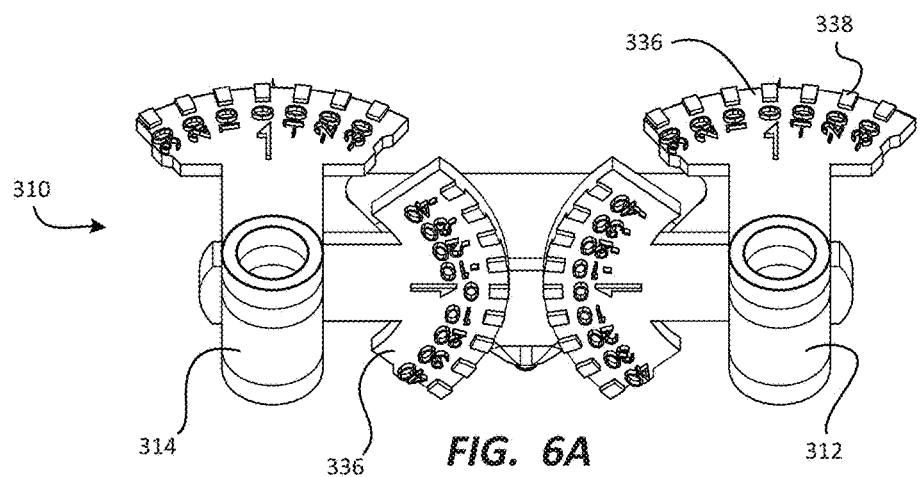
FIGS. 6A-6C are plan, front elevation, and perspective views, respectively, of a targeting system according to another embodiment of the present disclosure.
Figure 6B:
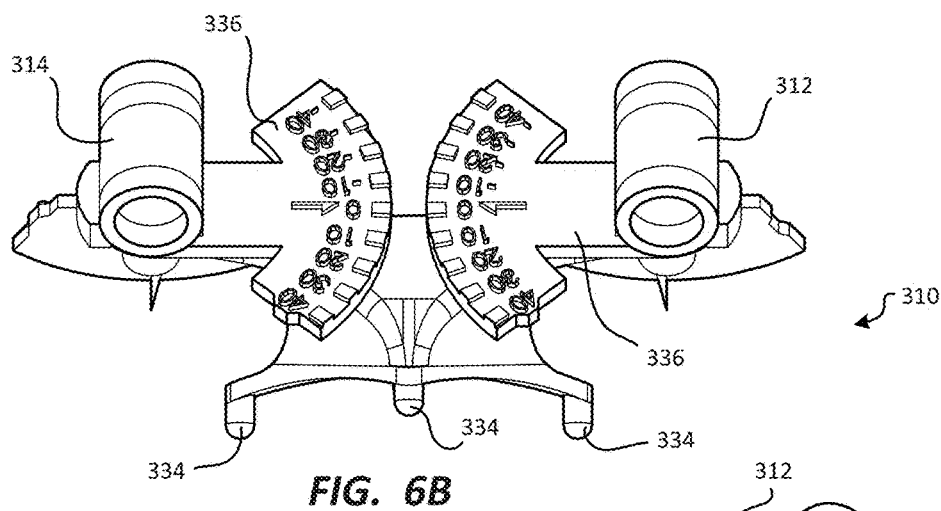
Figure 6C:
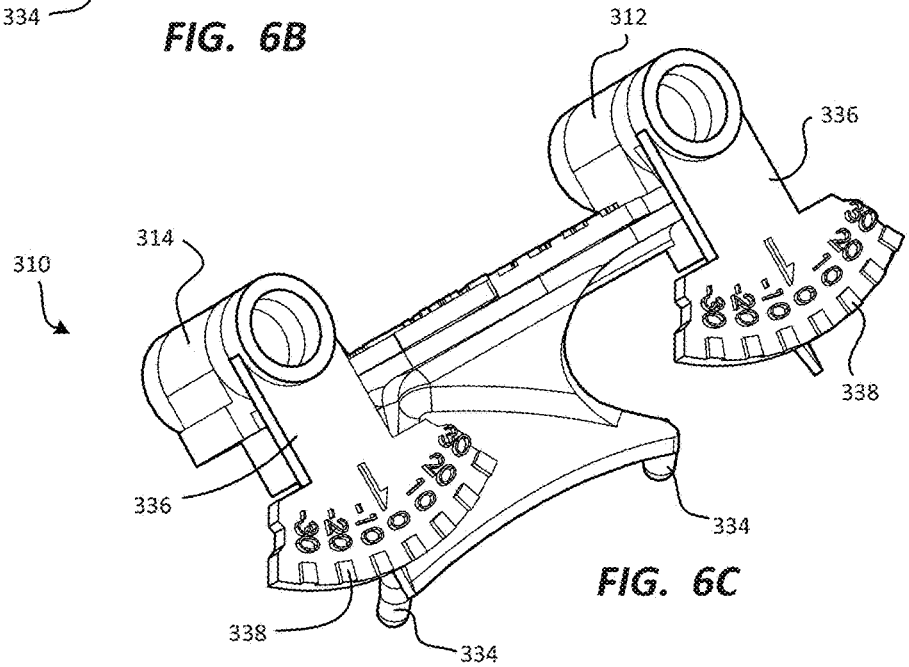
Figure 7A:
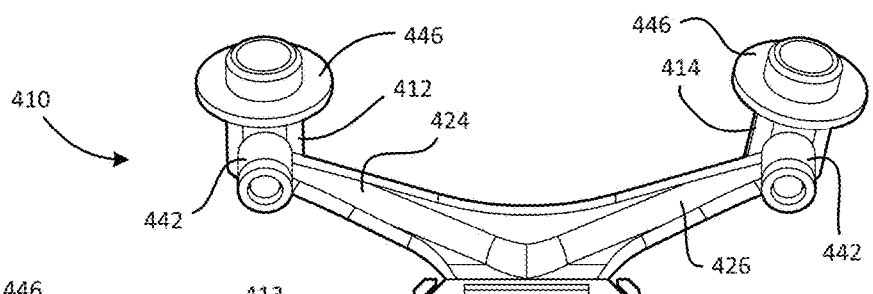
FIGS. 7A-7D are front elevation, perspective, plan, and side elevation views, respectively, of a targeting system according to yet another embodiment of the present disclosure.
Figure 7B:
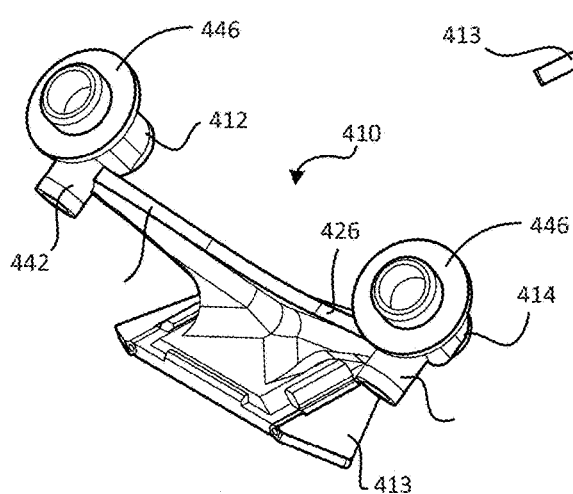
Figure 7C:
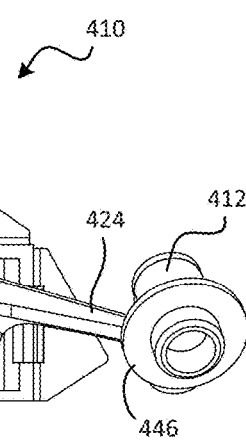
Figure 7D:
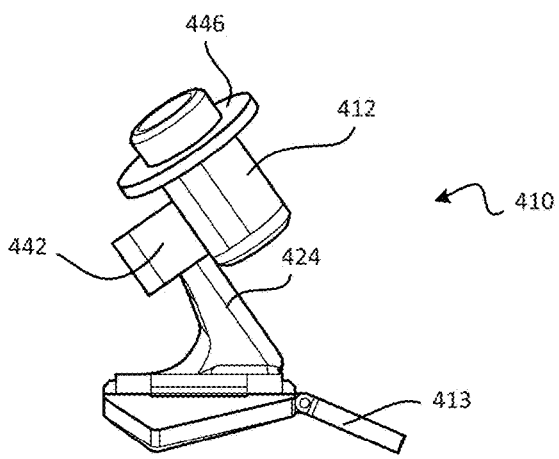

Referring to FIGS. 6A-6C, plan, front elevation, and perspective views, respectively, illustrate a targeting system, or system 310, according to another embodiment. The system 310 may have a first laser 312 and a second laser 314, and may provide for manual adjustment of the orientations of the first laser 312 and the second laser 314. Additionally, the system 310 may have feet that mate with a plurality of fiducial markers (not shown) on the patient. Such fiducial markers may be attached, for example, through the aid of a baseplate 228 such as that of FIGS. 5A-5B, as set forth above. The feet may take the form of posts 334, which may register in such fiducial markers or other registration attachments.

In one example, as illustrated in FIGS. 6A-6C, the system 310 may also include angle indicators 336, which may take the form of precision-machined discs. The first laser 312 and the second laser 314 may each be rotatable in the "roll" and "yaw" directions, and may be fixed in the "pitch" direction. Thus, the angle indicators 336 may also be referred to as "roll" and "yaw" angle indicators. The angle indicators 336 may have pre-determined radii with markings 338 etched, embedded, or otherwise provided to indicate the magnitude of the angle. The roll angle and/or the yaw angle of each of the first laser 312 and the second laser 314 may be adjusted to the desired number mechanically by rotating the first laser 312 and the second laser 314 around the roll axis and/or the yaw axis. Once a desired angle has been obtained, a locking mechanism such as setscrews or locking screws may be engaged to lock the system 310 into the desired configuration.

Referring to FIGS. 7A-7D, front elevation, perspective, plan, and side elevation views, respectively, illustrate a targeting system, or system 410, according to yet another embodiment. The system 410 may have electronic angle readout and automated (motorized) laser angle adjustment in combination with a first arm 424, second arm 426, and base component 413 similar to that of FIGS. 3A-3C.

In the system 410 of FIGS. 7A-7D, rotary encoders 442 may be used to couple a first laser 412 and a second laser 414 to the first arm 424 and the second arm 426, respectively. The rotary encoders 442 may provide digital read-outs of the angle measurements (i.e., orientations) of the first laser 412 and the second laser 414. In this example, the first laser 412 and the second laser 414 may be connected to a controller (not shown in FIGS. 7A-7D), which may have a signal processing unit. Such a controller may be a dedicated module, a computer, a smartphone, a tablet, or the like. The controller may provide power to the first laser 412 and the second laser 414 and the rotary encoders 442, and may also receive the orientation output from the rotary encoders 442. In this application, the term "controller" does not require that a device issue operational commands to other components; rather, a controller may be any type of electrical device that interfaces with one or more other components of a targeting system.

Such a controller may additionally or alternatively control the orientation of the first laser 412 and the second laser 414 by transmitting signals to motors that rotate the first laser 412 and the second laser 414 to the desired orientation. In some embodiments, the controller may be connected to a first set of motors that controls the orientation of the first laser 412, and a second set of motors that controls the orientation of the second laser 414. Such motors will be shown and described subsequently, and may include servo motors, stepper motors, and the like. Such motors may be coupled directly to the first laser 412 and the second laser 414, or may be connected to them via gears or other torque-transmitting mechanisms. Alternatively, the controller may be connected to one or more mirrors or prisms (including MEM's micro-mirrors) that controls the orientation of the beam of light from the first laser 412, and one or more mirrors or prisms (including MEM's micro-mirrors) that controls the orientation of the beam of light from the second laser 414. In the case of motorized lasers, the desired angle may be digitally entered or controlled by a software program (for example, a program or app that runs on the controller), and the motors may drive the rotation of the laser units in the roll, pitch, and/or yaw directions. Another embodiment may integrate a motorized unit into the lens 16 of the first laser 412 and the second laser 414 to perform micro adjustments directly to the lens 16. This may be done in place of, or in addition to, mechanical roll, pitch, and/or yaw orientation adjustments of the first laser 412 and the second laser 414 and/or adjustments of the laser beams due to mirrors, prisms, or MEM's micro-mirrors. In alternative embodiments, a user may manually set the orientations of the first laser 412 and the second laser 414, as described previously.

In yet another example, the system 410 may include a built-in power source such as a battery. The system 410 may also have a wireless communication interface that wirelessly transmits the angle readings from the rotary encoders 446 to a controller or other electronic device in order to display them to the user. Automated control of the orientations of the first laser 412 and the second laser 414 may also be accomplished wirelessly. Any known wireless protocol may be used for communications between the first laser 412, the second laser 414, and the controller.

Targeting systems according to the present disclosure may be attached to other structures besides those of the patient's anatomy. Any stable structure may provide a suitable anchoring point for a fixture of a targeting system. It may be particularly advantageous to secure a targeting system to a medical imaging device. This may facilitate integration of such targeting systems with medical imaging because the locations of the light sources, relative to the imaging device, may remain constant. This may remove the need for fiducial markers to be used in imaging, even for medical imaging systems with movable components such as C-arm X-ray machines.

Figure 8:
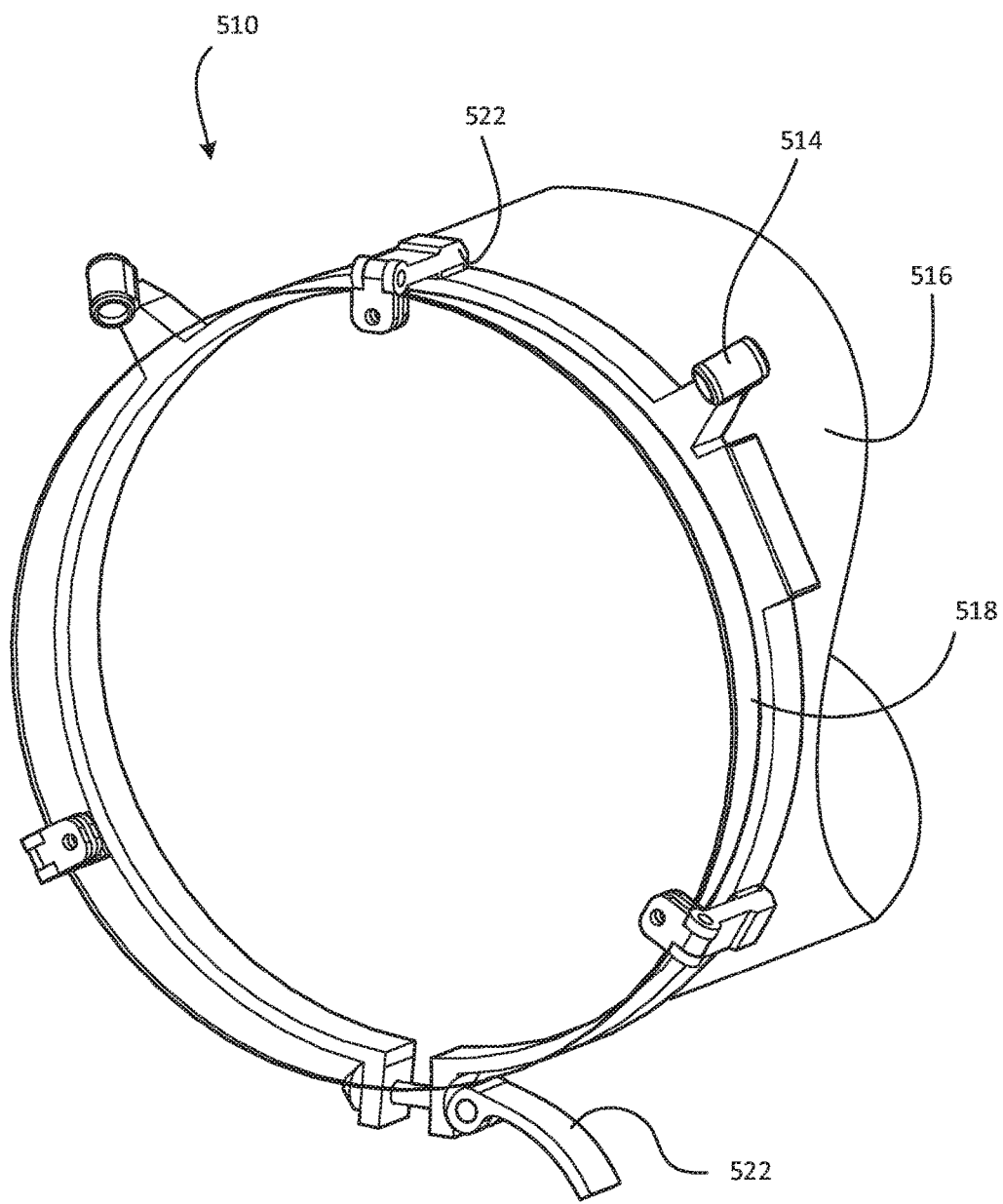
FIG. 8 is a perspective view of a targeting system for planar imaging modalities with attachment directly to a medical imaging device.

Referring to FIG. 8, a perspective view illustrates a targeting system, or system 510, according to yet another embodiment. The system 510 may be usable for planar imaging modalities with attachment directly to a medical imaging device. For example, the system 510 may be attached to an image intensifier 516 on a fluoroscopy unit. The fluoroscopy unit is used here to facilitate understanding of the concept, and should be understood as a specific embodiment of any general imaging device that takes projections of its subjects from a plurality of angles. The system 510 may readily be adapted for use with other imaging devices such as flat panel charge coupled devices (CCD's).

Figure 9A:
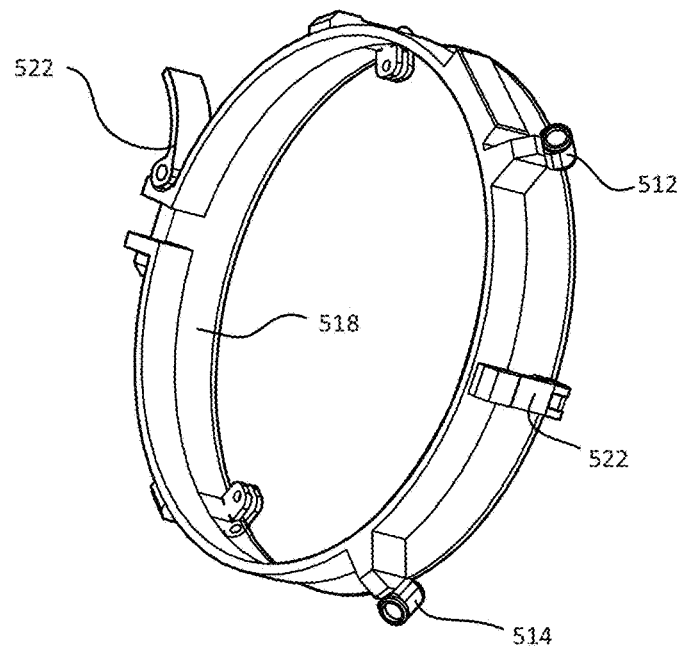
FIGS. 9A-9B are perspective and plan views, respectively, of the targeting system of FIG. 8.
Figure 9B:
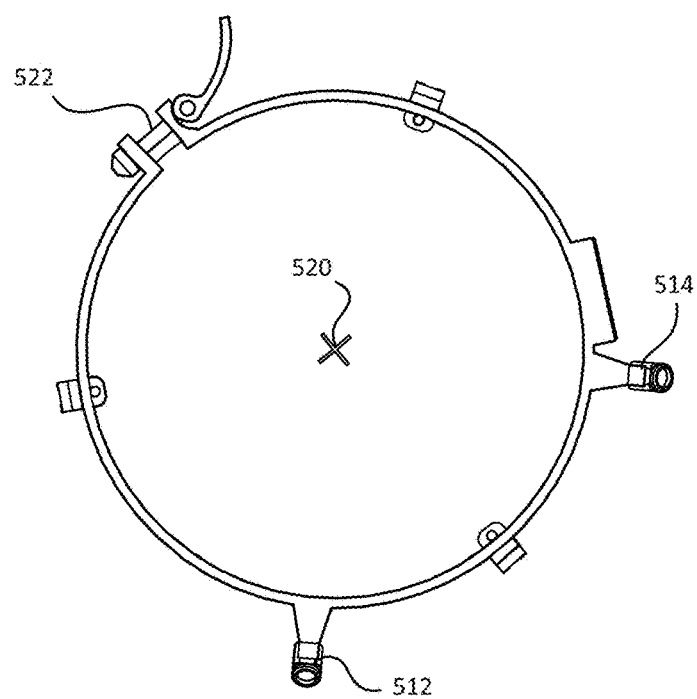

Referring to FIGS. 9A-9B, perspective and plan views, respectively, illustrate the system 510 of FIG. 8. As shown, the system 510 may include a first laser 512 and a second laser 514, both of which may be mounted to the image intensifier 516 via a fixture. In the system 510, the fixture may take the form of a ring 518, which may be concentric with the image intensifier 516 and secured to the image intensifier 516 via locking mechanisms such as screws, snaps, adhesives, or a quick-release mechanism 522. In known medical imaging devices, the image intensifier 516 may be expected to range from 9-11 inches in diameter; however, the image intensifier 516, and therefore the ring 518, may be larger or smaller than this. The ring 518 may extend about the entire circumference of the image intensifier 516, or may be a split ring or other structure that extends around a portion of the circumference of the image intensifier 516.

The first laser 512 and the second laser 514 may be attached to the ring 518, and the orientations of the first laser 512 and the second laser 514, relative to the ring 518, may be manually and/or electronically adjustable, as described in connection with the exemplary embodiments of FIGS. 6 and 7. In addition, the distance between first laser 512 and the second laser 514 along the ring 518 may be adjustable, as long as an accurate measurement of such distance can be obtained and accounted for in the angle calculation algorithm.

The system 510 may also include additional light sources, which may be additional lasers. Whether two or more lasers are used, the lasers may be mounted around the image intensifier 516 in such a way that the intersection of the light emitted by the lasers produces the targeting line. The targeting line may be coincident with the central axis of the imaging device, but is not limited to this configuration. The first laser 512 and the second laser 514 may be used to visualize the planned trajectory via projection of the targeting line, and a third laser at oblique angles to the first two lasers may be used to further specify an angle of rotation about the targeting line, a depth of insertion of a surgical instrument along the visualized trajectory, or the like. A third laser may also be used in combination with the first laser 512 or the second laser 514 to produce a second targeting line coplanar with the first targeting line. The second targeting line may be positioned to intersect the first targeting line to specify a single point in three-dimensional space. If a fourth laser is added, then two separate (not necessarily coplanar) targeting lines may be produced simultaneously. The latter example can also be used to specify the angle of rotation around a first targeting line, and depth of insertion along the first targeting line, simultaneously. A marker 520, which may be radio-opaque, may optionally be centered over the image intensifier 516 and secured to the ring 518. This marker 520 may help to identify the center of the image intensifier 516 and may be aligned with the axis of the X-ray tube.

The light sources may be either fixed in place relative to the image intensifier 516, or movable relative to the image intensifier 516. Fixed lasers, based on the example derived from the system 510, may be placed 90 degrees apart from each other to increase accuracy. Movable lasers may be also be used with C-arm based CT scanners. These systems may rely on the principle of cone-beam CT scanning and may swing the C-arm through 180 degrees to obtain an accurate three-dimensional dataset. Some C-arm based CT scanners are portable and some are fixed to the room they are installed in. The laser guidance system can be attached to part of the C-arm (e.g. flat panel detector, image intensifier, X-ray tube, or the arm itself). The 3-D dataset can be used to plan the trajectory. Based on knowledge of spatial location of the C-arm and the desired trajectory, the orientations of the first laser 512 and the second laser 514 can be calculated to reproduce the desired trajectory in physical space.

Figure 10:
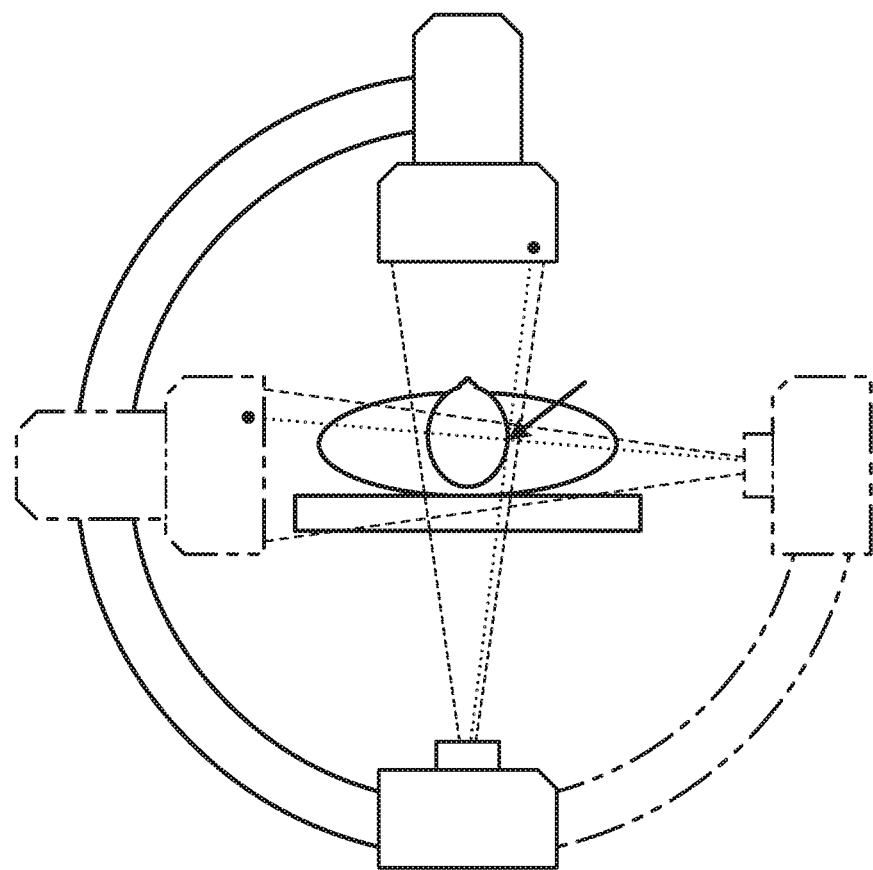
FIG. 10 is a front elevation view of an operating table, patient, and a trajectory to be visualized with a targeting system attached to a C-arm fluoroscopy unit. The C-arm fluoroscopy unit is illustrated in two orthogonal imaging positions.

Referring to FIG. 10, a front elevation view illustrates an operating table and patient with a trajectory to be visualized with a targeting system attached to an imaging device in the form of a C-arm fluoroscopy unit, illustrated in two orthogonal imaging positions. As an extension of the embodiment of the laser targeting system in the setting of planar imaging modality, methods for trajectory planning and angle calculation are developed. The imaging device in the form of a C-arm fluoroscopy unit is used for illustration purposes, but the concept can be generalized to any planar imaging modality utilizing penetrating radiation (e.g. monoplane or biplane angiography units). The solid black outline shows the imaging device taking an image at one position. The phantom outline shows the imaging device taking a second image after rotating 90 degrees. The patient is illustrated here in supine position with feet pointed into the page. The cross at the center of the image marks the idealized center of rotation of the imaging device. The two planar image projections are related to each other via the common center of rotation. Thus, during image acquisition, the imaging device may only be allowed to undergo pure rotation.

The dashed lines show the extent of radiation field captured by the image intensifier. The intersection of the two cones of radiation (triangles in FIG. 10 due to lack of 3-D perspective) marks the space (also referred to as the navigable space) that is used by the targeting system for trajectory planning and angle calculation. The solid black arrow simulates an external pointer with a tip pointing at an idealized entry site, which may represent a trajectory to be visualized. The dotted lines show the back projections of the pointer tip at each C-arm position extending from the radiation source to the image intensifier. The intersection of the two lines marks a unique point in the navigable space. Slight errors in the imaging device (structural deformation, epicyclic center of rotation, vibration etc.) may result in the dotted lines not meeting at a point, in which case a point in the navigable space that is the shortest distance to both of the lines can be used with an error term appended.

In a similar fashion, a second point in the navigable space (for example, another point on the trajectory) can be chosen to fully define the trajectory. The trajectory may be defined with respect to the imaging device. Likewise, the orientation calculations for the first laser and the second laser may also be carried out with respect to the imaging device once proper attachment and calibration is performed for the system. In at least one embodiment, no patient reference is needed during this planar imaging modality and accuracy should not be affected as long as the patient is not moved between image acquisition and trajectory visualization.

Figure 11A:
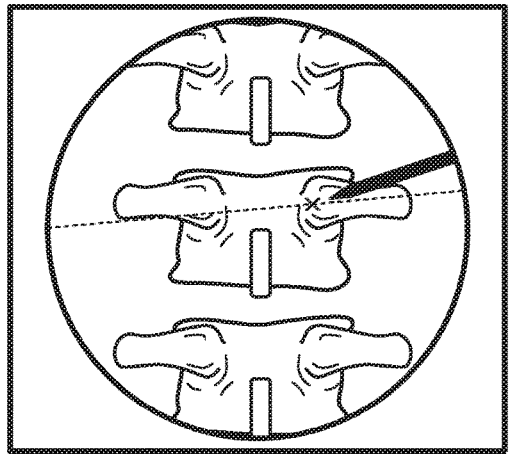
FIGS. 11A-11B are dorsal and lateral views, respectively, of a spinal procedure using a planar imaging modality that illustrate how orthogonal images can be used for trajectory planning and visualization.
Figure 11B:
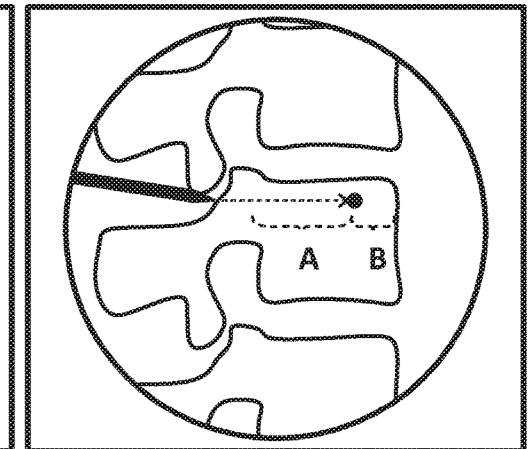

Referring to FIGS. 11A-11B, dorsal and lateral views, respectively, illustrate how orthogonal images can be used for trajectory planning and visualization with a targeting system for a spinal procedure using a planar imaging modality. FIGS. 11A and 11B illustrate the planning of a trajectory of a pedicle screw insertion. Two orthogonal images of the spinal column—dorsal and lateral—are taken and shown on the left and right screens. The black pointer rests at the ideal entry site—in this case at the lateral posterior margin of the pedicle. On the lateral projection, the ideal depth may be chosen and marked by the black dot. The dashed arrow shows the trajectory on the lateral projection. As an example, the ratio of A:B can be set to 2:1 to prevent anterior breach of the vertebral body. The dot may be back projected on the dorsal view as a dotted line.

To fix the target point, the user may choose the ideal target on the dorsal view, which is shown here as the medial edge of the pedicle (the X). This may be done to prevent medial breach of the pedicle. With entry and target points defined, the targeting system (such as the system 510 described previously) now has enough information to calculate the orientations of the first laser 512 and the second laser 514 needed to project a targeting line indicative of the desired trajectory. The imaging device may be locked at a particular angle (0 degrees, 90 degrees, or any angle in between) and this measurement may be provided to the system 510 to finalize the laser orientation calculation.

Figure 12A:
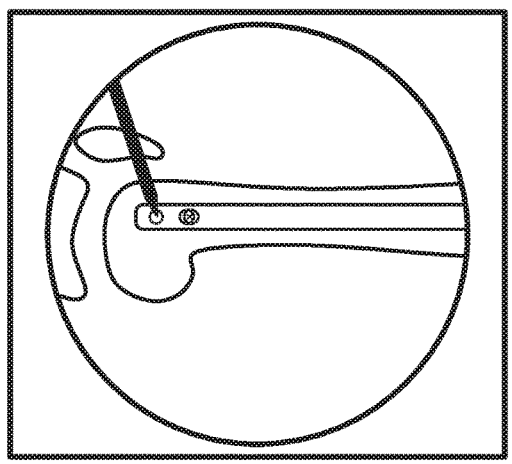
FIGS. 12A-12B are lateral and dorsal views, respectively, of an orthopedic procedure using a planar imaging modality that illustrate how orthogonal images can be used for trajectory planning and visualization in a laser targeting system.
Figure 12B:
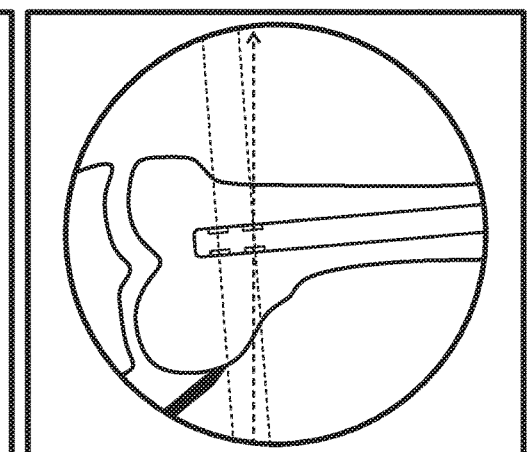

Referring to FIGS. 12A-12B, lateral and dorsal views, respectively, illustrate how orthogonal images can be used for trajectory planning and visualization with a laser targeting system for an orthopedic procedure using a planar imaging modality. FIGS. 12A-12B illustrate an orthopedic procedure involving distal locking of an intramedullary nail. Two orthogonal images may be taken. The image on the left shows an "ideal hole" next to a shifted hole as is often the case due to divergent radiation paths from the beam source. The black pointer may rest at the center of the ideal hole. The back projection through the hole, from the radiation source to the image intensifier, may provide the ideal path for the distal locking screw. This back projection can be digitally added to the image on the right, as is shown by the dashed line. The dashed line may go through the tip of the black point, and any discrepancy can be added to the error term.

Based on the available information, a trajectory may be formed and laser angles can be calculated. However, the trajectory of the adjacent hole can also be obtained to save procedural time and reduce radiation exposure to patient and house staff. The left image may be used again and the center of the shifted hole can be selected (e.g. via the centroid method, represented by the X). The back projection is shown on the right image as the dashed arrow. Since the holes are parallel to each other, the trajectory from the previous hole may be used. The intersection of the two trajectories (dashed arrow and dashed line) at the midline of the screw (lengthwise) on the right allows for accurate targeting of the second hole. The imaging device may be locked at a particular angle (0 degrees, 90 degrees, or any angle in between) and this measurement may be provided to the targeting system (for example, the system 510) to finalize the calculation of the orientations of the first laser 512 and the second laser 514.

Figure 13:
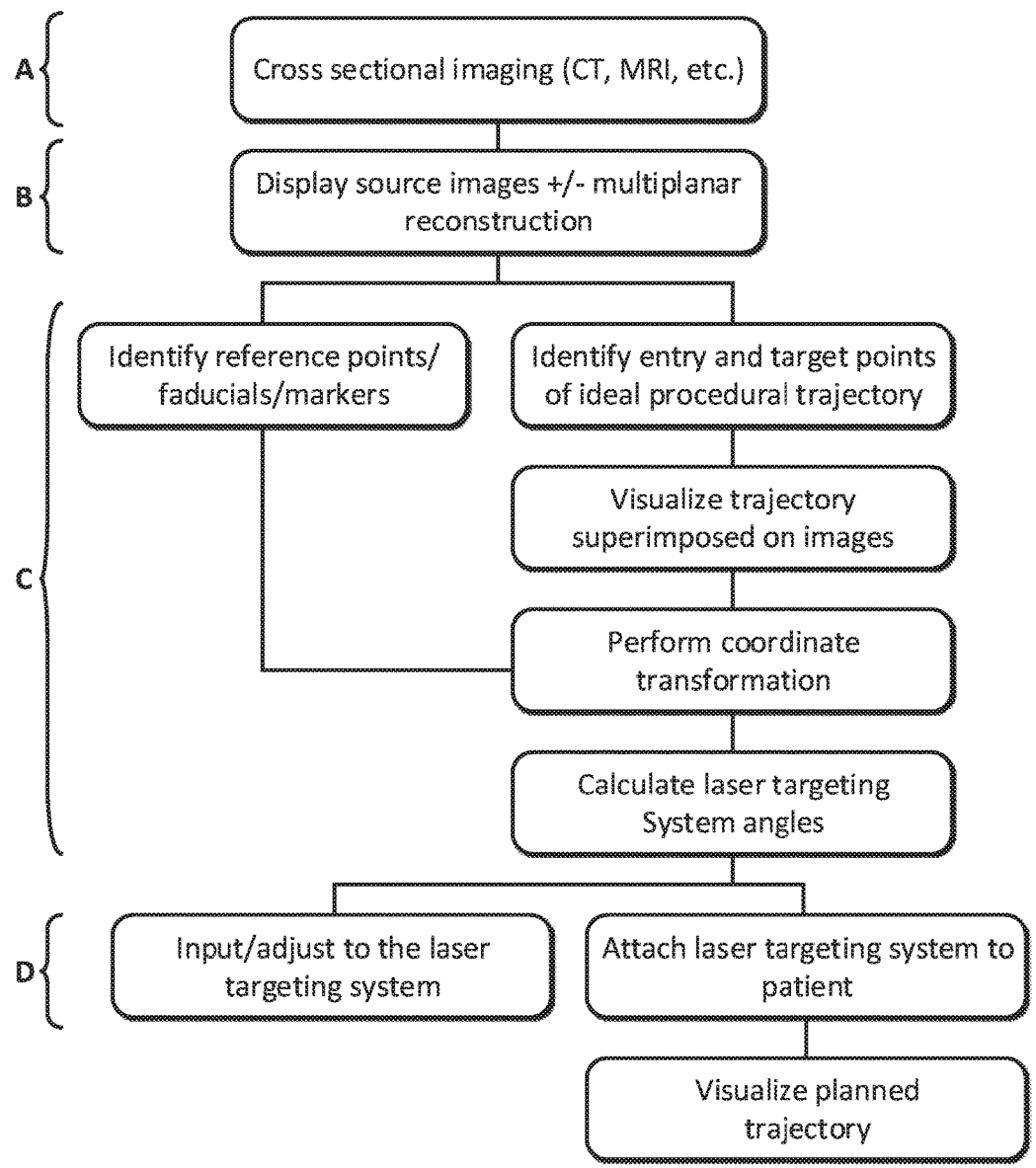
FIG. 13 is a block diagram illustrating one method of using a targeting system in a cross-sectional imaging modality with one or more reference markers attached to a patient.

Referring to FIG. 13, a block diagram illustrates one method of using a targeting system in a cross-sectional imaging modality. The method will be described in connection with the system 10 of FIGS. 1-3C, but may be carried out with any targeting system within the scope of the present disclosure. The method may commence with obtaining the image with or without reference marker(s) attached to the patient (step A). The source images, as well as any multiplanar reconstructions, may be displayed. There are a number of options for this step, including but not limited to: an imaging device terminal such as a CT suite (e.g. CT suite), a diagnostic unit such as a Picture Archiving and Communication System (PACS) unit, or a computer or electronic device (e.g. tablet) capable of displaying Digital Imaging and Communications in Medicine (DICOM) format images (step B).

A software interface may be employed by the user to perform trajectory planning and angle calculations. This can be done either on the same system as step B or on a different system capable of displaying the acquired images. The software interface may be set up to facilitate the flow of image registration (which may also be referred to as reference identification), entry/target point identification, trajectory planning/visualization, and finally laser angle calculation (step C).

One example of the software embodiment of step C may involve the identification of either fiducial markers or baseplate markers such as the posts 234 of FIGS. 5A-5B by the software. The software may automatically calculate the transformation matrix required to perform a coordinate transformation of the image space onto the laser targeting system space. The operator may select the entry point and the target on the cross-sectional image. Multi-planer reconstruction views may be presented to facilitate identification of the most optimal entry/target points. Once the two points are selected, a line in the 3-dimensional image space may be constructed which represents the desired trajectory. This line may be transformed into the targeting space of the system 10 using the previously derived transformation matrix. The software may calculate the unique combination of orientations of the first laser 12 and the second laser 14 such that the first light 18 and the second light 20 intersect to produce the targeting line 22 in 3-D space representing the desired trajectory.

Another example of the software embodiment of step C may involve generation of a trajectory from a set of orthogonal X-ray images. For many orthopedic procedures such as hip/knee arthroplasty or trauma surgery, cross-sectional imaging, such as CT scanning, may not be routinely available. However anterior-posterior (AP) and lateral X-rays may be a routine part of the workup for many patients, and intraoperative fluoroscopy can take films in views which are 90 degrees apart. After attaching the reference marker (fiducials or baseplate), two X-rays may be taken 90 degrees apart. The end user may identify target points on both X-rays. Once this is done, a set of x, y, z values may be calculated. An additional rotational and scaling transformation may be applied to one of the films in order to generate a truly orthogonal coordinate system in the targeting space of the system 10. The ideal trajectory projections may be identified by the end user on the two films, bearing in mind that the trajectory lines identified on the two films are projections of a unique 3-D trajectory onto 2-D space. The backward projections of the two 2-D lines form two planes perpendicular to each of their reference planes and the intersection of these two planes form a unique trajectory line in 3-D space. The unique trajectory line in 3-D space may then be coordinate transformed into the targeting space of the system 10 and calculations of the laser angles can be carried out as previously discussed.

This method enables the calculation of a trajectory in 3-D space based on projections identified on two 2-D X-rays films orthogonal to each other. It does not specify the projection at any other arbitrary angle of view. For procedures that routinely use plain film X-ray's for follow-up, this is adequate to meet the user's needs since views at other angles are not routinely considered. Step D represents the last step required to visualize the target trajectory.

Figure 14:
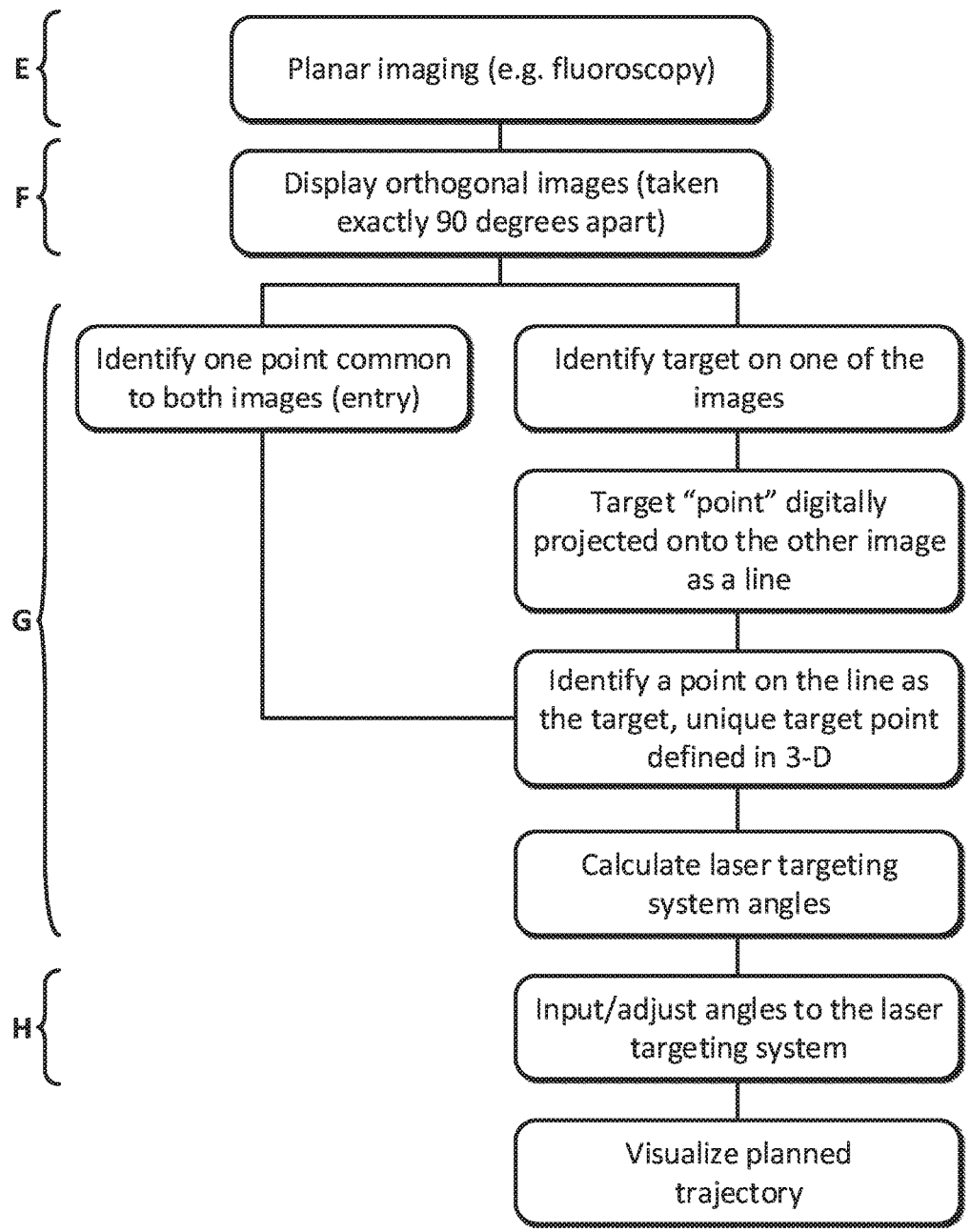
FIG. 14 is a block diagram illustrating one method of using a targeting system in penetrating planar imaging modalities with two or more images taken from orthogonal viewpoints.

Referring to FIG. 14, a block diagram illustrates one method of using a targeting system in penetrating planar imaging modalities with a minimum of two images taken from orthogonal viewpoints. A minimum of two orthogonal images of the anatomical area of interest may first be obtained as described in FIGS. 10-12 (step E).

The images may be displayed and options for display include, but are not limited to: the imaging device terminal (e.g. fluoroscopy screen), a diagnostic unit (e.g. PACS), a computer or electronic device (e.g. tablet) capable of displaying DICOM format images (step F).

A software interface may be used to perform trajectory planning and angle calculations. This can be done either on the same system as step F or on a different system capable of displaying the acquired images. The software interface may be setup to facilitate the flow of entry/target point identification, trajectory visualization, and finally laser angle calculation (step G). Examples of step G are provided in FIGS. 11 and 12 in accordance with their respective exemplary embodiments. Step H represents the last step for visualizing the target trajectory for the planar imaging modality. To help visualize the targeting line(s) and/or the appropriate depth of travel for a surgical instrument, a visualization guide may be used. Such a visualization guide may be used to facilitate viewing of the targeting line and/or guiding of a surgical instrument along the desired trajectory.

Figure 15:
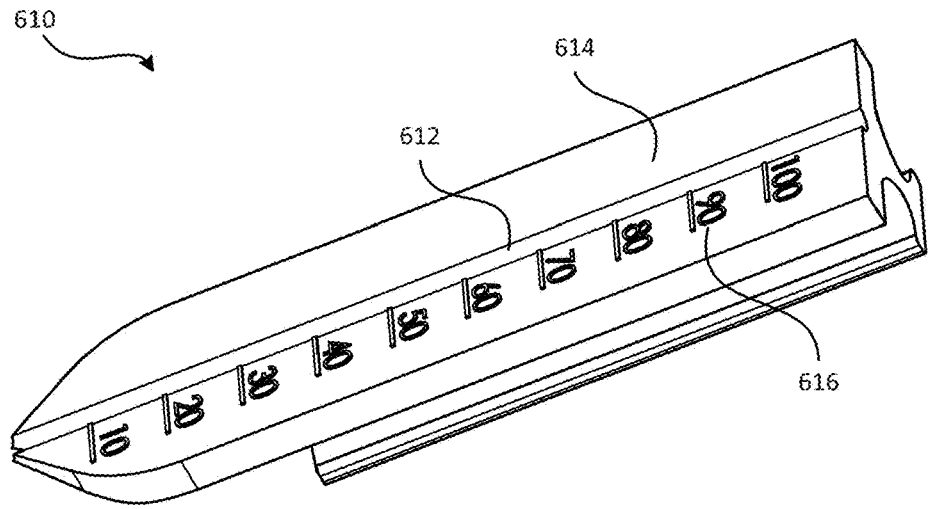
FIG. 15 is a perspective view of a visualization aid in the form of a grooved instrument guide with depth measurements.
Figure 16:
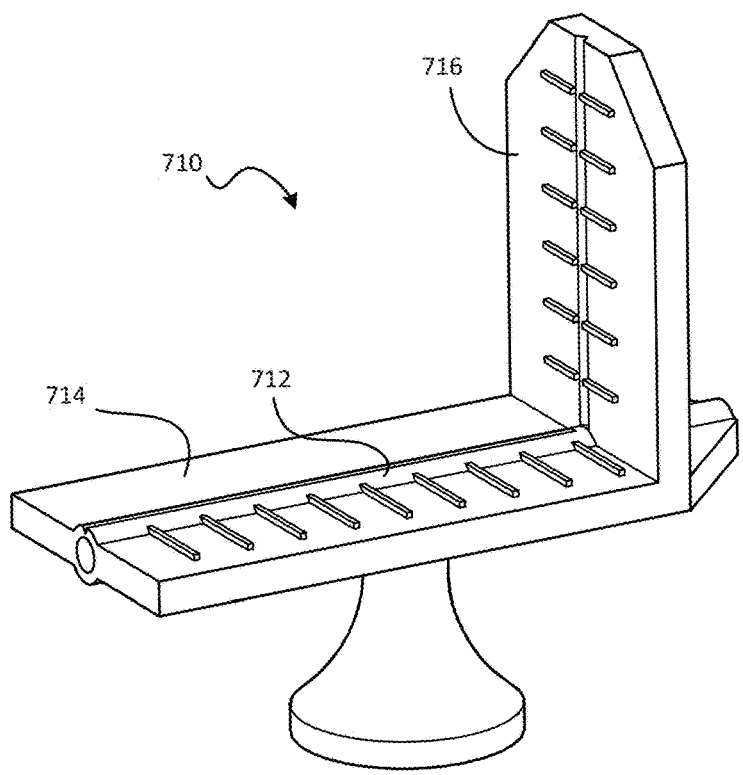
FIG. 16 is a perspective view of another visualization aid in the form of an enclosed channel and depth control for one or more targeting lines.
Figure 17:
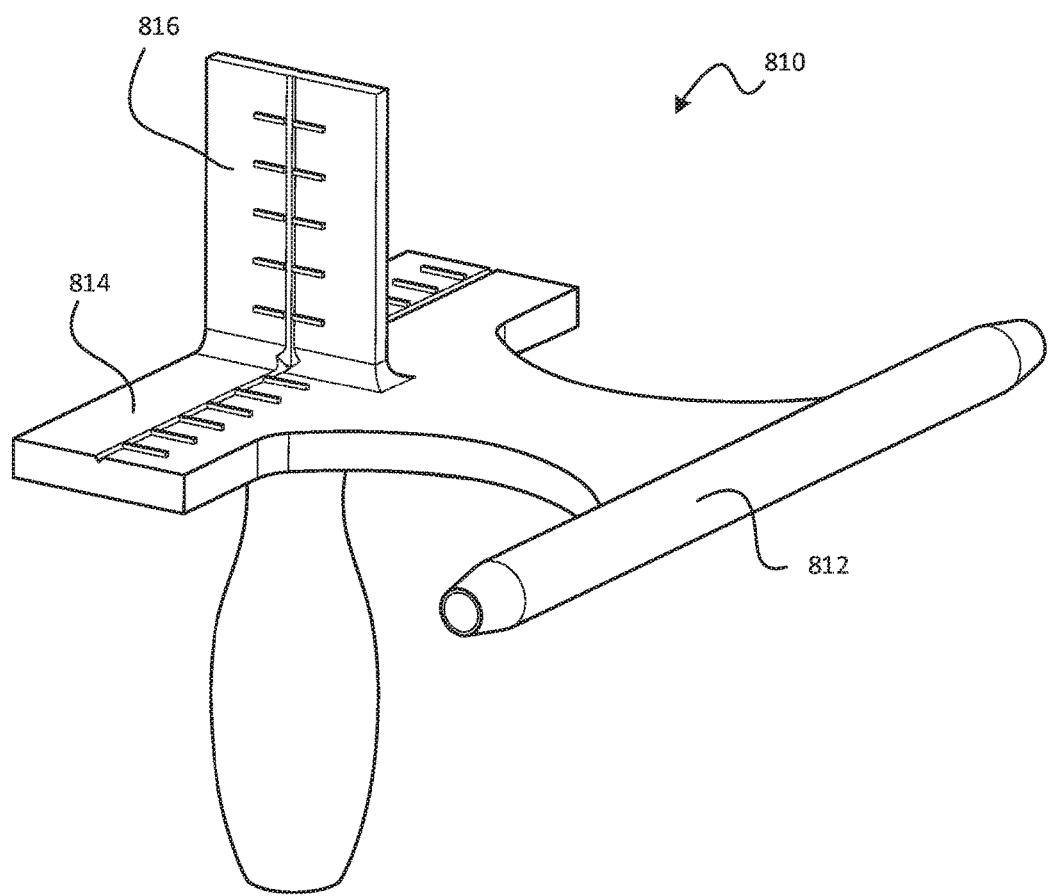
FIG. 17 is a perspective view of another visualization aid in the form of an offset enclosed channel and depth control for one or more targeting lines.

Referring to FIG. 15, a perspective view illustrates a visualization aid 610 in the form of a grooved instrument guide with depth measurement, according to one embodiment. The visualization aid 610 will be described in conjunction with the system 10 of FIGS. 1-3C, but may be used with a targeting system according to any embodiment within the scope of this disclosure, including those designed for cross-sectional imaging modalities, and those designed for planar imaging modalities.

The visualization aid 610 may further be a simple open-channel trajectory guide. The visualization aid 610 may thus have a guide surface 612 in the form of an open channel that may be used to conduct a surgical instrument, such as a needle, trocar, cannula, depth probe, implant, or the like, along the desired trajectory. The visualization aid 610 may further have a visualization surface 614 that extends on either side of the guide surface 612 with a widened shape on which the first light 18 and the second light 20, by way of example, may be projected and viewed.

The visualization surface 614 may optionally have a matted or otherwise textured surface that facilitates visualization of reflected light from a wide range of viewing angles. Further, the visualization surface 614 may optionally have depth markings 616 etched, scored, painted, or otherwise marked on the visualization surface 614 to facilitate proper insertion of the surgical instrument. The visualization surface 614 may optionally be white in color to provide for enhanced visibility of reflected light. In alternative embodiments, any color may be used. If the visualization surface 614 is colored, the color of reflected light by the visualization surface 614 may or may not match that of the light emitted by the first laser 12 or the second laser 14. The visualization surface 614 may alternatively be black to reduce glare from light interference. In such an event, the luminance provided by the first laser 12 and the second laser 14 may need to be increased to compensate for the increased light absorption of the black color. Additionally, the visualization aid 610 may be opaque, translucent, and/or transparent.

For embodiments with an opaque construction, the first light 18 and the second light 20 may reflect off of the visualization surface 614. Thus, the first light 18 may be visible on the visualization surface 614 as a first line, and the second light 20 may be visible on the visualization surface 614 as a second line with a color different from that of the first line. If the first and second lines are nonparallel, this may indicate that the visualization aid 610 needs to be reoriented. If the first and second lines are parallel, but displaced from each other, this may indicate that the visualization aid 610 needs to be translated toward or away from the first laser 12 and/or the second laser 14. As the first and second lines converge (i.e., the linear displacement and/or angular displacement between the first and second lines is reduced as needed), the targeting line 22 may become visible on the visualization surface 614 and/or the guide surface 612. Due to the additive properties of light, the targeting line 22 may have a color different form that of the first line and the second line. Thus, the convergence of the first and second lines and/or the appearance of the targeting line in the additive color may indicate that the visualization aid 610 is in the position and orientation of the desired trajectory.

For embodiments with a transparent or translucent construction, the first light 18 and the second light 20 may penetrate the body of the visualization aid 610 and, when the visualization aid 610 is aligned with the desired trajectory, this may cause the visualization aid 610 to glow in the additive color to confirm proper alignment of the visualization aid 610 with the desired trajectory. Thus, the visualization aid 610 may improve the visualization of the first light 18, the second light 20, and the targeting line 22, thereby easing the process of aligning a surgical instrument with the desired trajectory.

In addition, the guide surface 612 may also help to guide the insertion of devices. The depth markings 616 may allow the visualization of depth information during the insertion process. The visualization aid 610 may additionally or alternatively include features such as an enclosed tube, rail, channel, or other mechanical fitting that interacts with implants and/or surgical instruments to align those implants and/or surgical instruments with the desired trajectory.

In processes in which sterility is not of a critical importance, a device capable of atomizing water droplets, saline solutions, ringer's lactate, tissusol, or other suspended particulates in the air or fogs or fog-like states may be used. An ultrasonic transducer (not shown) submerged in sterile water or saline can create a cloud and a fan located above the ultrasonic transducer device can move the small water droplet across specially designed channels and ducts. This may create laminar airflow with a uniform volume of droplets to reflect the laser light. Such procedures may enable direct visualization of the targeting line 22 in the suspended particulates or vapor without the need for a flat surface to reflect the light.

To further aid the visualization process, one or more fiber optic features can be incorporated into the guide surface 612. The light from the targeting line 22 may be directed down the fiber optic tract to further aid visualization. Additional electronic components can also be incorporated into the trajectory guide to analyze the light intensity and colors. For example, a photo diode, charged couple device (a rectangular grid or line-type CCD), or other CMOS sensor(s) may be used to monitor incoming light. The signal output can provide feedback to the user regarding accuracy of trajectory alignment. Furthermore, in alternative embodiments, the visualization aid 610 may be incorporated into other medical devices, such as the body of an ultrasound probe or surgical instrumentation set (e.g. drill, screwdriver, rod holder etc.) to provide direct visualization of the trajectory.

Referring to FIG. 16, a perspective view illustrates another visualization aid 710 in the form of an enclosed channel and depth control, which may help visualize the primary targeting line as well as a secondary targeting line projected from one or two additional light sources of the targeting system. As shown, the visualization aid 710 may take the form of a trajectory guide with a guide surface in the form of the bore of an enclosed tube 712 with a visualization surface 714 on either side of it. Further, the visualization aid 710 may have an orthogonal alignment piece 716 that may be used for visualization of a secondary targeting line or other feature projected by one or more additional light sources (for example, a third and/or fourth laser).

The visualization surface 714 may function in a manner similar to that of the visualization surface 614 of the visualization aid 610 of the previous embodiment. The enclosed tube 712 may be used to guide surgical instruments such as catheters, needles, drills, and the like. The orthogonal alignment piece 716 may be perpendicular to the tube 712 and may provide visualization of a third and/or fourth light source.

For example, a third laser that projects light nonparallel to the first light 18 and nonparallel to the second light 20 can be used. The intersection of this third laser with the targeting line can be visualized on the orthogonal alignment piece 716. This alignment may define the degree of rotation along the desired trajectory, thereby fixing another degree of freedom. The amount of rotation along the planned trajectory can be planned on the cross-sectional or planar imaging, and the third light source can be moved accordingly once the appropriate calculations are performed.

If a fourth laser is added, then the intersection of the third and fourth lasers may form a second targeting line. The orientations of the light sources can be calculated such that this second targeting line intersects with and/or is orthogonal to the first (primary) targeting line formed by the first laser 12 and the second laser 14. This may not only lock in rotation, but may also provide depth visualization. This may also add control of another degree of freedom in the depth direction along the desired trajectory.

Referring to FIG. 17, a perspective view illustrates another visualization aid 810 in the form of an offset enclosed channel and depth control. The visualization aid 810 may facilitate visualization of the primary targeting line as well as a secondary targeting line projected from one or two additional light sources of the targeting system, while providing an actual trajectory offset from the targeting line(s).

The visualization aid 810 may have a guide surface including a bore of an enclosed channel 812. In alternative embodiments, the visualization aid 810 may instead have a guide surface with an open channel, a series of rings, and/or or any number of features that allow the visualization aid 810 to be used to guide instruments and/or implants. The visualization aid 810 may be similar to that of FIG. 16 in that the targeting line 22 may be visualized in addition to a secondary targeting line or other features that provide visualization of orientation and/or depth control, depending on the number of light sources used in the targeting system. The visualization aid 810 may thus have a visualization surface 814 and an orthogonal alignment piece 816, which may function in a manner similar to their counterparts of FIG. 16.

The visualization aid 810 may position the enclosed channel 812 at any desired distance and/or orientation with respect to the visualization surface 814 and the orthogonal alignment piece 816, as long as this orientation is known beforehand and factored into the calculations. In alternative embodiments, the angular and/or linear displacement between the guide surface and the visualization surface may be made adjustable, and the relative positioning of the visualization and guide surfaces can be accurately measured and accounted for in the calculations. If any adjustment to the relative orientation and/or position of the guide surface and the visualization surface occurs after performance of the calculations, a new set of measurements may be taken and calculations may be performed again.

Any of the visualization aids disclosed herein may be made to attach to the patient or a targeted object in a wide variety of ways. Various attachment mechanisms may be employed, depending on the surface properties of the attachment site, including adhesives, hook and loop fasteners such as Velcro™, pins, screws, clamps, jaws, etc.

Alternatively or additionally, a separate stand and/or support arm may be provided to hold the visualization aid in place. This may be a standalone unit with its own stand and adjustable arm to aid positioning and/or keep the visualization aid in place. Alternatively or additionally, such an adjustable support arm can be made attachable to an operating room table, an imaging device (e.g. a C-arm), or any suitable feature on the targeted object.

Such a support arm can be further motorized and integrated with a robotic control system to provide a semi-automated or fully-automated alignment process. Such systems can be connected to the controller mentioned above to allow communication with the user. Additionally or alternatively, such a support arm can be incorporated into a robot-assisted procedure as outline above.

The visualization aid may be further adjustable with respect to the attachment base/arm system. A locking mechanism may be provided, and may have a set screw, thumb screw, clips, quick release mechanism, and/or other mechanism that provides releasable locking to secure the visualization aid in the desired configuration once the appropriate alignment is obtained. This may free the hand(s) of the operator from holding the visualization aid securely at all times to allow the operator to focus on the procedure itself.

Figure 18:
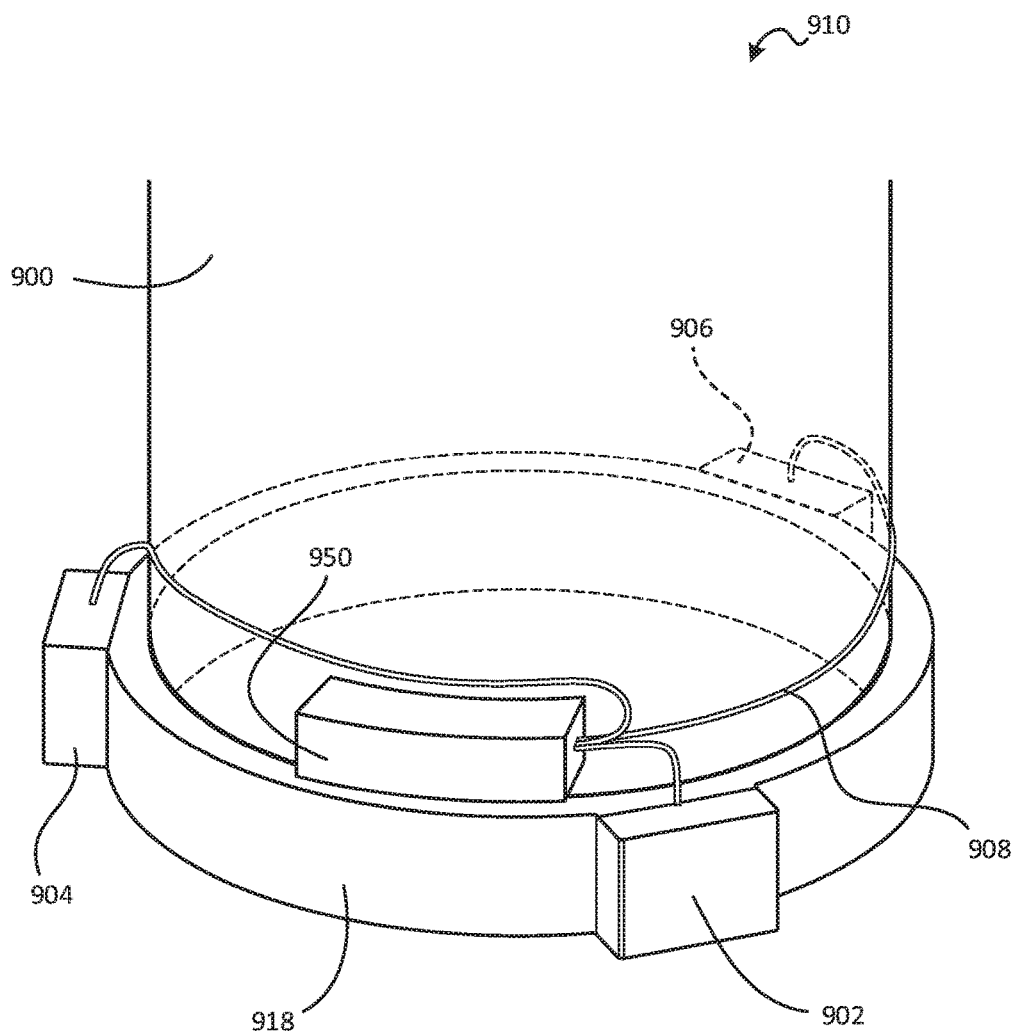
FIG. 18 is a perspective view of a targeting system according to another embodiment of the present disclosure.

Referring to FIG. 18, a perspective view illustrates a targeting system, or system 910, according to another alternative embodiment of the disclosure. Like the system 510 of FIGS. 8-9B, the system 910 may be designed for attachment to a medical imaging device, such as the imaging intensifier 900 of a C-arm fluoroscopy unit. The system 910 may include a first light source in the form of a first light module 902, a second light source in the form of a second light module 904, and a third light source in the form of a third light module 906. The system 910 may also include a fixture in the form of a ring 918, and a controller 950.

The first light module 902, the second light module 904, and the third light module 906 may each be fixedly secured to the ring 918. The first light module 902 may contain a first light source (not shown) such as a first laser, and may also contain a first set of motors (not shown) capable of changing the orientation of the first laser. Similarly, the second light module 904 may contain a second laser (not shown) and a second set of motors capable of changing the orientation of the second laser. Further, the third light module 906 may contain a third laser (not shown) and a third set of motors capable of changing the orientation of the third laser. Hence, although the first light module 902, the second light module 904, and the third light module 906 may be substantially rigidly attached to the ring 918, the corresponding light sources may be oriented at the necessary orientations to provide visualization of a desired trajectory.

As shown, the controller 950 may be electrically coupled to the first light module 902, the second light module 904, and the third light module 906 via wires 908. The controller 950 may receive data from the first light module 902, the second light module 904, and the third light module 906, including data representative of the actual orientations of the first, second, and third lasers. Additionally or alternatively, the controller may transmit signals to the first light module 902, the second light module 904, and the third light module 906 to activate the first, second, and third lasers and/or set the orientations of the first, second, and third lasers.

As mentioned previously, the use of more than two light sources may allow additional visualization to shown, such as the desired orientation and/or depth of a surgical instrument at the desired trajectory. Alternatively, the use of more than two light sources allows the optimal two light sources to be used. Thus, in the event that a light source is blocked or is not optimally positioned to provide accurate visualization of the desired trajectory, other light sources may be used instead. Positioning the first light module 902, the second light module 904, and the third light module 906 at an even distribution about the periphery of the image intensifier 900 may enhance the likelihood that at least two light sources of the system 910 will be unobstructed and positioned for accurate projection of the targeting line. In other embodiments, more than three light sources may be used.

Figure 19:
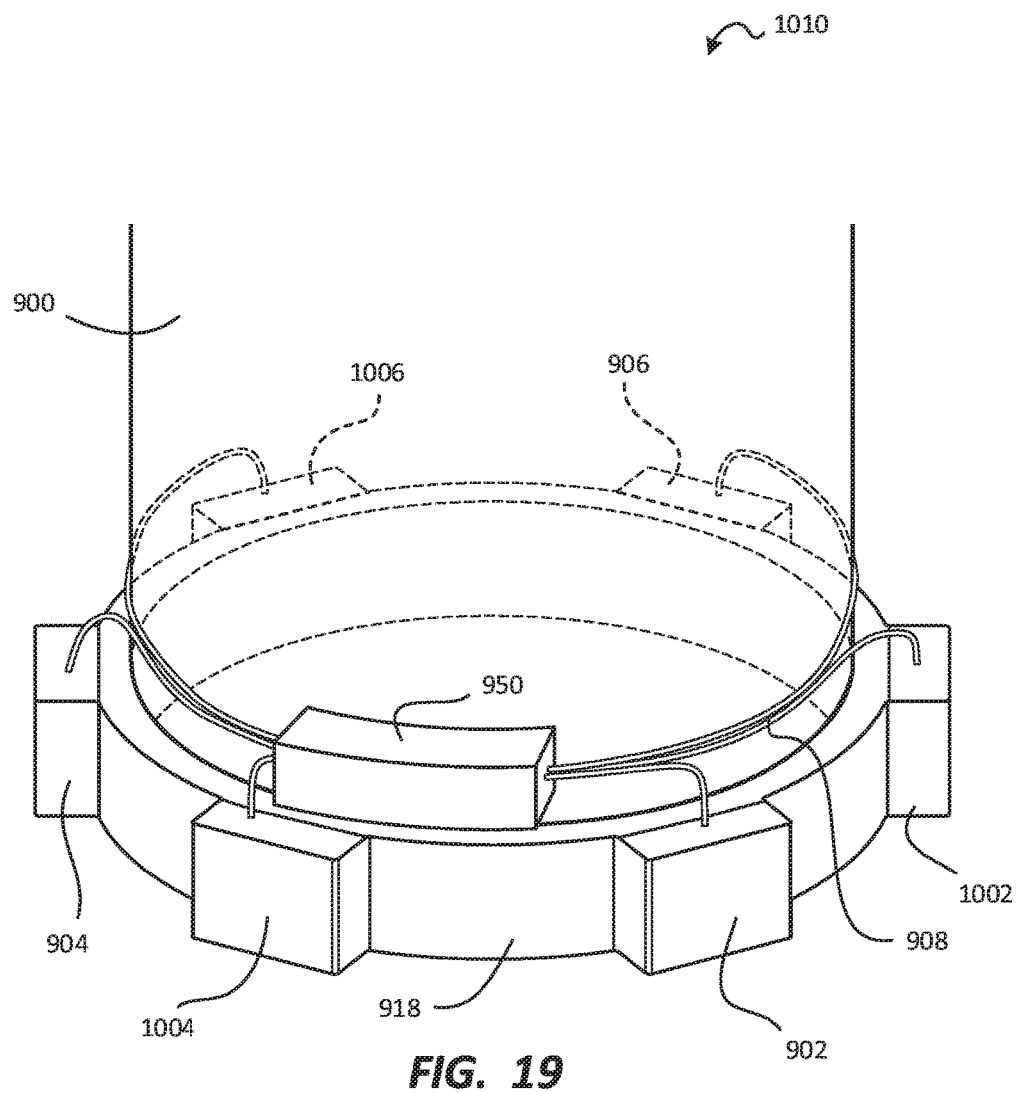
FIG. 19 is a perspective view of a targeting system according to yet another embodiment of the present disclosure.

Referring to FIG. 19, a perspective view illustrates a targeting system, or system 1010, according to another alternative embodiment of the disclosure. The system 1010 may have a configuration similar to that of the system 910, except that the system 1010 may have additional light sources. More specifically, in addition to the first light module 902, the second light module 904, and the third light module 906, the system 1010 may have a fourth light module 1002, a fifth light module 1004, and a sixth light module 1006. These may be fixedly attached to the ring 918, but may contain fourth, fifth, and sixth light sources, which may be fourth, fifth, and sixth lasers that are movable relative to the ring 918.

The use of six light sources may enable the projection of additional features and/or lines. Further, the use of six light sources may further enhance the likelihood that at least two light sources of the system 1010 will be unobstructed and positioned for accurate projection of the targeting line.

Figure 20:
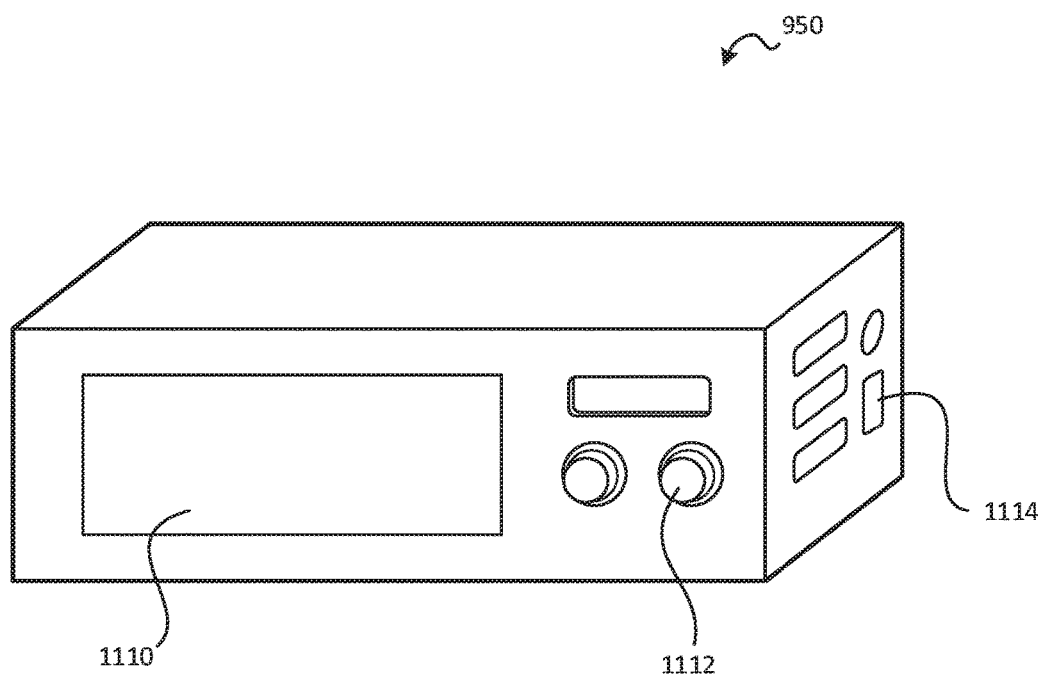
FIG. 20 is a perspective view of the controller of FIGS. 18 and 19.

Referring to FIG. 20, a perspective view illustrates the controller 950 of FIGS. 18 and 19 in greater detail. As shown, the controller 950 may have a display 1110, a control interface 1112, and connection ports 1114. The display 1110 may, for example, display the angulation of any or all of the light modules connected to it. Such data may come from the light modules. Additionally or alternatively, the controller 950 may have a built-in gyroscope, encoder or other measurement device that indicates the angle at which the controller 950 is positioned. When used on a mobile platform such as a movable medical imaging device, the mobile platform may be moved back to a datum position (for example, the first position at which imaging data was captured) in order to provide a meaningful indication of orientation. Furthermore, should such controller be mounted on an X-ray image intensifier, the planar X-rays could be position-locked to the orientation of the system to facilitate both calibration and trajectory planning/targeting.

The control interface 1112 may be used by the user to change the settings of the system 910, the system 1010, or manually key in the orientations of the light sources, turn light modules on or off, manually enter the position and/or orientation of the desired trajectory, or the like. The connection ports 1114 may be used to connect the controller 950 to other components such as the light modules, the medical imaging device to which it is attached, an external computer, or the like. If desired, the controller 950 may receive orientation data for the light modules and/or the desired trajectory directly from the medical imaging device or an external computer. Thus, the controller 950 may be designed to operate independently of any direct user input.

Figure 21A:
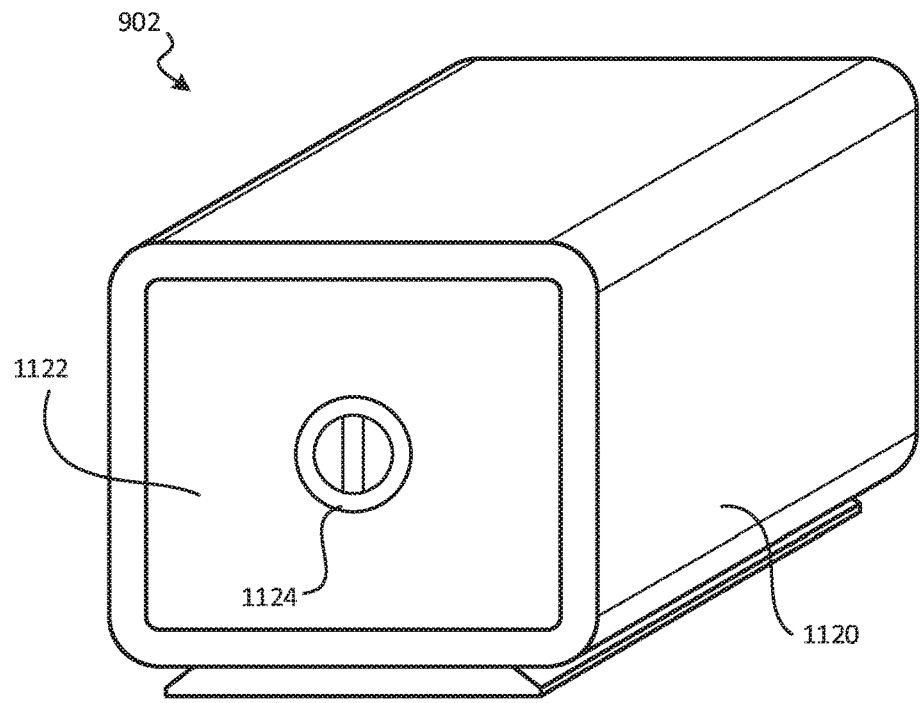
FIGS. 21A and 21B are perspective and front elevation section views, respectively, of the first light module of FIGS. 18 and 19.
Figure 21B:
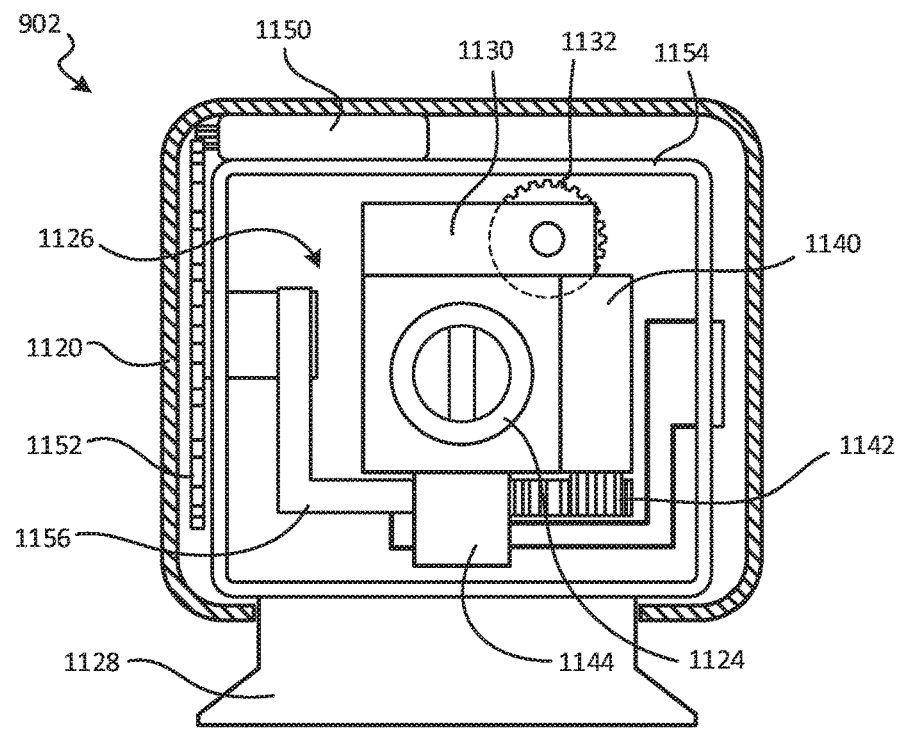

Referring to FIGS. 21A and 21B, perspective and front elevation views, respectively, illustrate the first light module 902 of FIGS. 18 and 19 in greater detail. The first light module 902 may be substantially the same as the other light modules, i.e., the second light module 904, the third light module 906, the fourth light module 1002, the fifth light module 1004, and the sixth light module 1006.

The first light module 902 may have a housing 1120 with the overall shape of a rectangular prism. The housing 1120 may be formed of a polymer if desired, for the purpose of limiting the weight of the targeting system. The housing 1120 may be hollow, and may contain a first light source, which may be a first laser 1126 as mentioned previously. The first laser 1126 may have a slotted cap 1124 that causes the light emitted by the first laser 1126 to propagate along a plane, i.e., the first plane as discussed in connection with FIG. 1.

The first light module 902 may also have a window 1122 that is translucent to permit light from the first laser 1126 to exit the housing 1120. If desired, the window 1122 may be tinted to act as a filter. Thus, the window 1122 may, if desired, be used to determine the wavelength(s) of light that form the first light emitted by the first light module 902. The window 1122 may only permit light of a certain wavelength range to exit the housing 1120. Alternatively, the first laser 1126 may be designed to emit light of the desired color. In such a case, the window 1122 may not be tinted, and need not act as a filter.

As shown in FIG. 21B, the first light module 902 may also have an attachment interface 1128 designed to facilitate removable, yet secure attachment of the first light module 902 to the ring 918. The attachment interface 1128 may take the form of a dovetail base that mates with a corresponding undercut slot (not shown) formed in the ring 918. In alternative embodiments, other fastening systems may be incorporated into an attachment interface, including but not limited to screw-mounted systems, slidable quick-release systems, and the like.

The first light module 902 may have a first set of motors that controls the orientation of the first laser 1126 within the housing 1120. For example, the first set of motors may include a roll control motor 1130, a yaw control motor 1140, and a pitch control motor 1150. The roll control motor 1130 may adjust the "roll" orientation of the first laser 1126, the yaw control motor 1140 may adjust the "yaw" orientation of the first laser 1126, and the pitch control motor 1150 may adjust the "pitch" orientation of the first laser 1126.

The pitch control motor 1150 may be positioned adjacent to an internal frame 1154 within the housing 1120. The internal frame 1154 may contain a swivel bracket 1156 that is pivotably connected to the internal frame 1154 such that the swivel bracket 1156 can rotate within the internal frame 1154 to permit adjustment of the pitch of the first laser 1126. The pitch control motor 1150 may be coupled to the swivel bracket 1156 via pitch control gearing 1152, so that rotation of an output shaft of the pitch control motor 1150 causes the swivel bracket 1156 to angle the first laser 1126 upward or downward, relative to the view of FIG. 21B.

The yaw control motor 1140 may be positioned on the swivel bracket 1156, adjacent to the first laser 1126. The first laser 1126 may be pivotably coupled to the swivel bracket 1156 via a transverse shaft 1144. The transverse shaft 1144 may rotate to permit the first laser 1126 to rotate leftward or rightward, relative to the view of FIG. 21B. The yaw control motor 1140 may be coupled to the transverse shaft 1144 and/or the adjacent portion of the swivel bracket 1156 via yaw control gearing 1142. Rotation of an output shaft of the pitch control motor 1150 may cause the first laser 1126 to rotate relative to the swivel bracket 1156.

The roll control motor 1130 may be positioned above the first laser 1126. The roll control motor 1130 may be coupled to the first laser 1126, or to just the slotted cap 1124, via roll control gearing 1132. Thus, rotation of an output shaft of the roll control motor 1130 may cause the first laser 1126 and/or the slotted cap 1124 to roll about an axis perpendicular to the page, with respect to the view of FIG. 21B.

As mentioned previously, a light source need only have an adjustable orientation about two orthogonal axes. However, providing orientation adjustment about all three axes may provide for additional flexibility in the operation of the targeting system. If desired, any one of the roll control motor 1130, the yaw control motor 1140, and the pitch control motor 1150 may be omitted, if desired, to immobilize the first laser 1126 as applied to rotation about the corresponding axis.

Figure 22A:
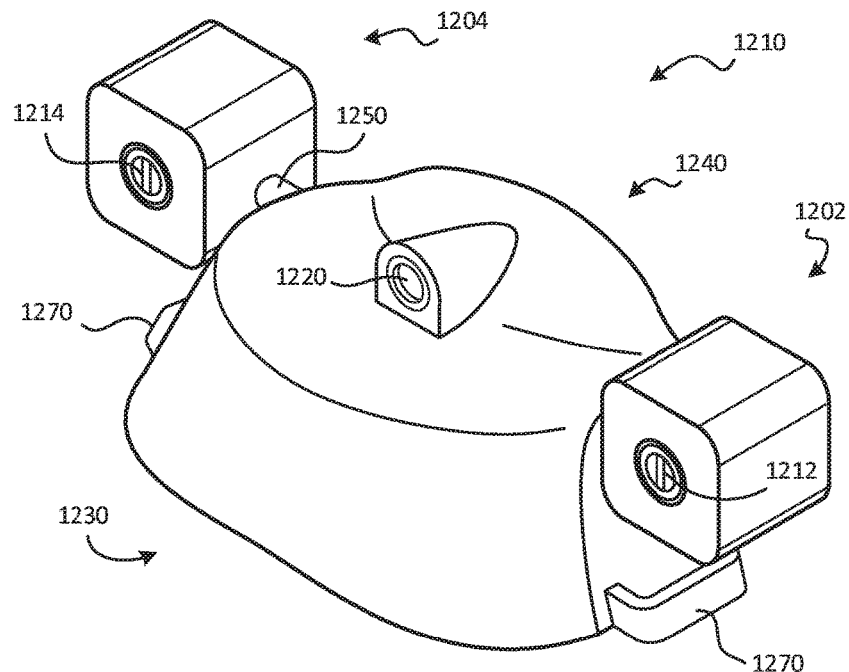
FIGS. 22A and 22B are perspective and front elevation section views, respectively, of an alternative targeting system embodiment of the present disclosure including an image-capture device.
Figure 22B:
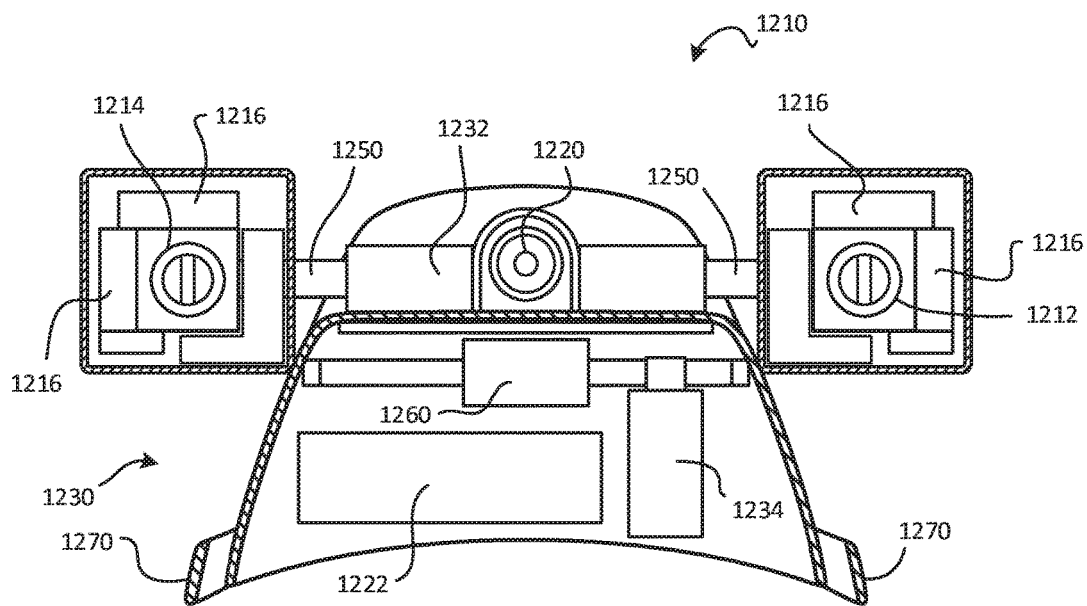

Referring to FIGS. 22A and 22B, perspective and front elevation, section views, respectively, illustrate a targeting system, or system 1210, according to another alternative embodiment of the disclosure. An image-capture device may be integrated into the system 1210. The image capture device may take the form of a camera 1220 mounted to the body of the system 1210. The camera 1220 may include various imaging technologies, including but not limited to CCD (charge coupled display) sensors, CMOS (complementary metal-oxide-semiconductor) sensors, and the like. Digital output from the camera 1220 may facilitate the operation of the system 1210, but in alternative embodiments, analog and/or film-based cameras may be used. For procedures that require a targeting system to be mounted on the patient, the system 1210 depicted in FIGS. 22A and 22B may represent a fiducial-free method of obtaining accurate registration.

Additionally, the system 1210 may have a fixture in the form of a base unit 1230, an armature 1240, and laser mounting posts 1250 on the armature 1240, on which a first laser module 1202 and a second laser module 1204 may be mounted. The camera 1220 may be coupled to the armature 1240, which may be movable relative to the base unit 1230. The first laser module 1202 may have a first laser 1212 that is rotatable within the first laser module 1202 about at least two of the roll, pitch, and yaw axes described previously. Similarly, the second laser module 1204 may have a second laser 1214 that is rotatable within the second laser module 1204 about at least two of the roll, pitch, and yaw axes. Motion of the first laser 1212 and the second laser 1214 within the first laser module 1202 and the second laser module 1204 may be accomplished through the use of motors 1216, as shown in FIG. 22B.

The base unit 1230 may be securable to an external structure adjacent to the patient, including but not limited to armature, pole, platform, and the like. The base unit 1230 may also be securable to a portion of the patient's anatomy. Where the system 1210 is to be used for a cranial procedure, such as installation of an EVD, the base unit 1230 may be secured to cranial anatomy, such as the forehead. For other procedures, the system 1210 may be attached to a different location on the patient. As mentioned before, locations with relatively little soft tissue covering the underlying bone may provide optimal locations for registration. This may facilitate the use of attachment features in the form of non-invasive attachment mechanisms 1270 to attach the system 1210 to the patient, such as straps, grips, adhesives, and/or the like. Additionally or alternatively, if desired, the system 1210 may be secured through soft tissue to underlying bone through the use of screws or other devices.

The camera 1220 may be positioned at a known distance from the first laser module 1202 and the second laser module 1204. The first laser module 1202 and the second laser module 1204 may project first light and second light (not shown) along first and second planes (not shown), respectively to provide a targeting line. When projected onto a surface, such as a portion of the patient's anatomy, the first light, the second light, and/or the targeting line may reflect off of the surface of the patient's anatomy. The reflection, including any attendant distortion, may be captured by the camera 1220. Through triangulation, given the known positions of the first and second planes relative to the camera 1220, the system 1210 may determine the coordinates, in three-dimensional space, of the anatomical features intersecting the first light and the second light. Thus, at a given angle between the first laser 1212 and the camera, the triangulation process produces a line of information in 3-D space. By scanning the laser line across an object and capturing images at each angle increment, a full three-dimensional dataset can be built-up that accurately represents a 3-D surface.

In FIG. 22A, the first laser module 1202 may be connected to a controller 1222. The system 1210 may use the first laser module 1202 and/or the second laser module 1204 to scan across the patient's anatomical region of interest. The laser light may be rotated about a single axis at set degree intervals (for example, yaw at 5 degree intervals) and the camera 1220 may capture an image at each such interval. The controller 1222 may generate a three-dimensional map of the surface of the patient's anatomical region. This may be done, for example, by comparing the reflection of the first light, the second light, and/or the resulting targeting line to a pre-defined set of reference images saved in a database. This three-dimensional surface may then be matched to the three-dimensional surface generated from patient imaging (e.g., CT/MRI scans, or any other 3-D surface images). The trajectory planned using such imaging may be used in conjunction with the three-dimensional surface information to calculate the pitch, yaw and/or roll orientations of the first laser 1212 and the second laser 1214. The first laser module 1202 and the second laser module 1204 may be set at the proper orientations and activated to produce a targeting line at the desired trajectory without the need of any fiducials attached to the patient.

One laser module (i.e., either the first laser module 1202 or the second laser module 1204) is sufficient to capture the necessary 3-D surface data from the patient. Both the first laser module 1202 and the second laser module 1204 may be used to improve the accuracy of the system and reduce "blind spots." When the first laser module 1202 and the second laser module 1204 are both used, the first laser 1212 may be scanned across the patient's anatomical region, followed by the second laser 1214. The images may be captured and processed, and the distortions of the reflections of the first light and the second light from the patient's anatomy can be matched to the respective databases of the first and second laser lines. The resulting cloud-point data can be added together, or reconstructed, to generate the final 3-D surface map.

In FIG. 22B, the controller 1222 may be connected to one or more motors that move the armature 1240 relative to the base unit 1230. The motors may include, for example, a pitch motor 1232 that controls the pitch of the armature 1240 relative to the base unit 1230, and a yaw motor 1234 that controls the yaw of the armature 1240 relative to the base unit 1230. The armature 1240 may be rotatably coupled to the base unit 1230 via a bearing 1260. The pitch motor 1232 may cause the laser mounting posts 1250 to rotate relative to the armature 1240. The first laser module 1202, the second laser module 1204, and the camera 1220 may be secured to the laser mounting posts 1250 such that rotation of the laser mounting posts 1250 causes the pitch of the first laser module 1202, the second laser module 1204, and the camera 1220 to change. The system 1210 may cause the pitch and/or yaw of the camera 1220, the first laser module 1202, and/or the second laser module 1204 to change and position the camera 1220 at the most optimal vantage point relative to the anatomical region of interest. This may improve the quality of the 3-D surface map and thence, improve the accuracy of registration of the system 1210 on the relevant anatomy and projection of the targeting line.

The system 1210 may also use image subtraction to further increase contrast of the laser line scan. The camera 1220 may first take an image of the anatomical area of interest without the first laser 1212 and/or the second laser 1214 turned on, thereby acquiring a baseline image. The first laser 1212 and/or the second laser 1214 may then be activated, and image acquisition may proceed at set degree intervals as described above. The baseline image may be subtracted from the acquired set of images to effectively eliminate background pixels, leaving only the reflected light from the first laser 1212 and/or the second laser 1214. To maximize registration accuracy, the patient's anatomical area of interest should have distinctive 3-D features. Since the facial area has many such distinctive features, the system 1210 is well adapted to cranial applications.

Figure 23:
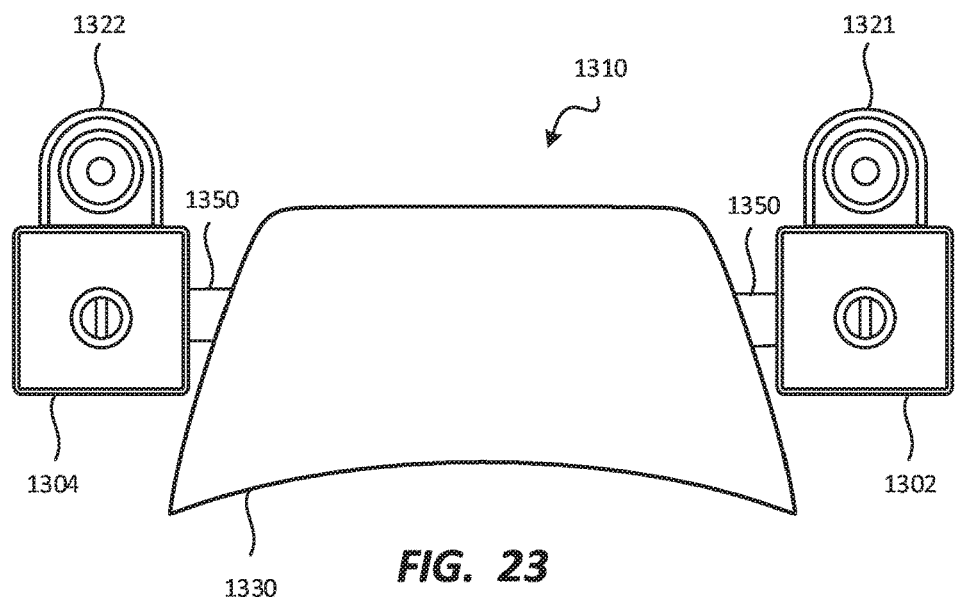
FIG. 23 is a front elevation view of a targeting system including multiple image-capture devices according to another embodiment of the present disclosure.

FIG. 23 illustrates a targeting system 1310 for providing visualization of a trajectory for a medical instrument, according to another alternative embodiment of the present disclosure. The targeting system 1310 may include an image capture system configured to capture image data of anatomical features of a patient at a first location in space. The targeting system 1310 may also include an illumination system configured to project light to indicate the trajectory. In at least one embodiment, the illumination system may include a first laser module 1302 and a second laser module 1304. The first laser module 1302 may also be referred to as the first light source and a second laser module 1304 may also be referred to as the second light source. The targeting system 1310 may also include a base unit 1330, laser mounting posts 1350, a controller (not shown) and, in at least one embodiment, a rotatable armature (not shown) that couples the first laser module 1302 and the second laser module 1304 to the base unit 1330.

In the embodiment shown in FIG. 23, the image capture system includes a first camera 1321 and a second camera 1322. The first camera 1321 and the second camera 1322 can be mounted a certain distance apart from each other to provide stereo-vision. The first camera 1321 and the second camera 1322 can be mounted to the first laser module 1302 and the second laser module 1304 as shown in FIG. 23. The first camera 1321 and the second camera 1322 may be attached to the support bracket of each laser module such that it remains fixed as the yaw and roll motors of the laser module rotate the laser to the desired position. The cameras in this instance would only move in the pitch direction. Alternatively, the first camera 1321 and the second camera 1322 can move with the laser modules in the yaw direction as well.

In at least one embodiment, the first camera 1321 may be coupled to the base unit 1330 and configured to capture first image data of anatomical features of the patient at a first location in space. The second camera 1322 may also be coupled to the base unit 1330 and configured to capture second image data of the anatomical features of the patient at the first location in space. The second camera 1322 may also be spaced apart from the first camera 1321 by a predetermined distance to form a stereoscopic camera system.

In alternative multi-camera embodiments (not shown), the cameras can be mounted on the control module, main frame, or any other fixed or moveable part of the system. This may entail mounting cameras to the base unit 1330, similar to the system 1210 of FIGS. 22A and 22B, except that multiple cameras may be mounted to the base unit 1330 at a fixed distance apart in place of the single camera 1220 of FIGS. 22A and 22B. This may allow the cameras to remain stationary while the lasers move in pitch, yaw, and/or roll. The distance between the cameras may be known precisely. Thus, images taken by the cameras may be combined together with existing calibration information to generate precise three-dimensional surface maps of objects in the field of view (FOV) of the cameras.

A fixed or semi-fixed camera relationship as described above (i.e. with the cameras mounted on a fixed part of the system as described above, or with the cameras mounted to the laser modules for motion with the lasers in one direction) may be better suited for stereo vision applications. This may be particularly desirable for tracking an object in real-time. The object to be tracked can have certain features on it that allows a machine-vision algorithm to easily extract such features and calculate orientation information from photo and/or video data captured from each camera. The information from both cameras may be combined to fully calculate the three-dimensional position and orientation of the object. The information can be passed to a computer and used in a manner that best facilitates trajectory visualization. This process may be used to facilitate procedures including, but not limited to:

Setting a new entry point for the desired target and recalculating the trajectory;

Inputting a trajectory and comparing it to the planned trajectory in a training scenario (i.e., comparing the present trajectory to an ideal trajectory);

Tracking a pointer, catheter guide, probe etc. and constantly updating the position and orientation of such a device on a display screen (in essence providing navigation mode in a traditional image guidance system);

Allowing the laser to follow the pointer, catheter guide, probe, etc. as it is moved over the patient's navigational space; and/or If registration using laser scanning is unsuccessful, using a probe as a tracing device to capture surface information for the purpose of image registration between different image data sets.

The configuration described earlier, whereby the camera moves with the laser in yaw and pitch, may be better suited for laser-line scanning. The addition of yaw movement allows more flexibility in positioning the laser/camera system to achieve the greatest accuracy. Two or more cameras may also allow scanning from multiple directions, thereby reducing the number of "blind spots" that can be a problem with a single camera system.

Another alternative embodiment of the camera system with a single or multiple cameras is the addition of said camera(s) to the control unit, laser module, or separate camera housing on part of an X-ray system such as the image-intensifier of a fluoroscopic C-arm. This allows for tracking of movement of X-ray tube with respect to the patient. The trajectory planning technique mentioned in FIG. 10 above relies on the use of isocentric orthogonal set of x-ray images for calculation. Certain obstacles may prevent true isocentric rotation of X-ray system including but not limited to patient positioning, equipment, environment etc. In addition, design of X-ray systems (e.g. C-arm's) may cause a small amount of shift/angulation of principle image axis due to deformation of structure and/or gravity as the X-ray is rotated from AP to Lateral positions. One way to correct for these additional movements may be to position-lock the X-rays taken by keeping tracking of rotation and translation of the X-ray unit with respect to the patient.

The camera system mounted on the X-ray unit could track a patient reference/fiducial marker (see FIG. 31 below) and may work in conjunction with the position sensing system (e.g. gyroscopic or encoder based) amount in the control unit described in FIG. 20. Two or more planar X-ray images can be used that do not have to be isocentric or even orthogonal, so long as the X-ray tube positions can be recorded along with the images (position-locked). With knowledge of rotation and translation, the images can be transformed according to calibration data obtained beforehand, and trajectory planning and targeting can be performed. This may further speed up the workflow of using planar X-ray units for targeting/guidance since the restriction on image acquisition can be removed.

The targeting system controller may be configured to receive image data and indicate the trajectory relative to the anatomical features of the patient. In at least one embodiment, the controller may be configured to receive the first image data and the second image data and generate a three-dimensional map of the anatomical features of the patient at the first location in space and, based on the three-dimensional map, determine a first orientation of the first light source and a second orientation of the second light source at which the first targeting line indicates the trajectory.

The image capture systems of the targeting system 1310 may be configured to capture image data of anatomical features of the patient (for registration with image space data taken pre/intra-operatively) in various ways. For example, image data (e.g., first image data and second image data) collected by the image capture system may indicate reflections of ambient light from the anatomical features of the patient. In another example, image data collected by the image capture system may indicate reflections of laser light (e.g., first light and second light projected from the first laser module 1302 and the second laser module 1304, respectively) from the anatomical features of the patient. In yet another example, image data collected by the image capture system may indicate reflections of a light pattern projected from a structured light reflecting off the anatomical features of the patient, as will be described in more detail below.

In at least one embodiment, the first camera 1321 may be configured to capture third image data of the anatomical features of the patient at a second location in space and the second camera 1322 may be configured to capture fourth image data of the anatomical features of the patient at the second location in space. In this embodiment, the controller may be configured to receive the third image data and the fourth image data and generate a three-dimensional map of the anatomical features of the patient at the second location in space and, based on the three-dimensional map, determine a third orientation of the first light source and a fourth orientation of the second light source at which a second targeting line indicates an updated trajectory. In this manner, the targeting system 1310 may be able to continuously track the patient's movements and update the targeting line trajectory accordingly to improve accuracy and robustness of the medical procedure. Moreover, 3-D scanning of the patient's anatomical features with the methods described above does not require the application of fiducials to the patient prior to medical scans (CT, MRI, etc.) in order to facilitate registration. This results in "fiducial free" registration, which helps speed up the overall medical procedure.

Figure 24:
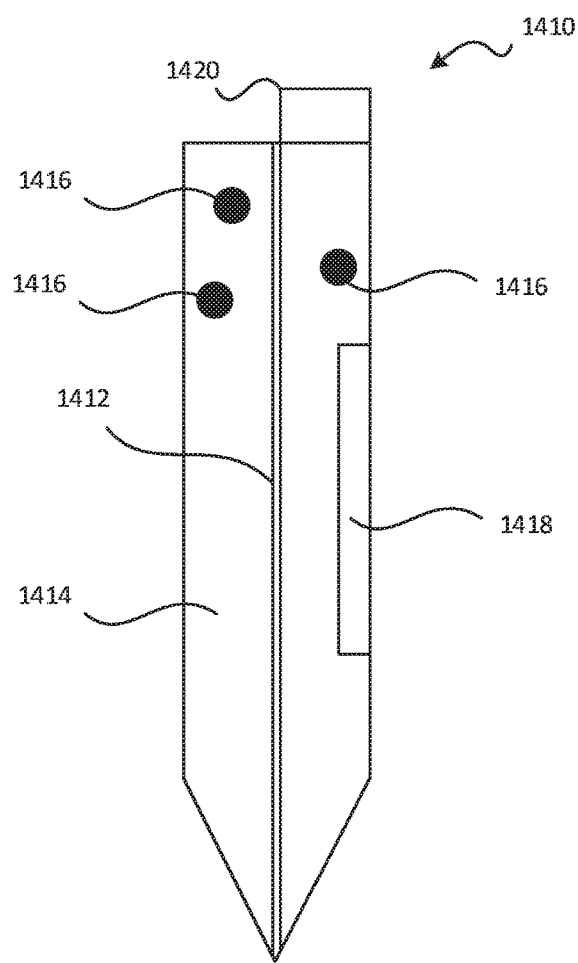
FIG. 24 is a side elevation view of a visualization aid including optical markers and geometrical features.

FIG. 24 illustrates an embodiment of a visualization aid in the form of a grooved instrument or guide probe 1410 with embedded features that allow the camera to easily visualize the position and orientation of the guide probe 1410. This may involve using one or more features with well-defined geometrical information. The guide probe 1410 may include a guide surface 1412, a visualization surface 1414 on which the first targeting line may be projected, one or more optical markers 1416 or unique patterned surfaces, and one or more geometrical features, such as notch 1418 and projection 1420. The camera may allow for tracking of the guide probe 1410 in the patient's space and translate this position information into the image space. This may allow for updating of anatomical information, as well as input from the user to select different entry and/or target point(s).

The guide surface 1412 may be in the form of an open channel that may be used to conduct a surgical instrument, such as a needle, trocar, cannula, depth probe, implant, or the like, along the desired trajectory. The guide surface 1412 may be positioned such that, with the first targeting line projected on the visualization surface 1414, the medical instrument may be slidable along the guide surface 1412 to move along the trajectory. The visualization surface 1414 may extend on either side of the guide surface 1412 with a widened shape on which the first light 18 and the second light 20, by way of example, may be projected and viewed.

In the embodiment shown in FIG. 24, the optical markers 1416 include three shaded or colored circles. However, it is understood that the optical markers on the guide probe 1410 can be any shape or color (e.g., square, triangle, rectangle, line, etc.), and may be present in any number. Furthermore they can even be a patterned surface, such as that shown in FIG. 31. By comparing the distortion (for example, linear transformation with rotation, shearing and scaling) to pre-defined geometrical information, position and orientation information may be calculated. This, can be performed with a single camera provided that the shape diameter and size is known and used in the calculation. Accordingly, such a guide probe may be used in conjunction with a single-camera system, similar to that shown in FIGS. 22A and 22B. However, using two or more cameras, as shown in FIG. 23, may improve the accuracy of such calculations. The optical markers may advantageously provide high contrast (for example, through the use of black-white interfaces, saturated colors, infrared reflective coatings, and/or the like). In addition to or in the alternative to the optical markers, the guide probe 1410 may also have unique geometrical features, as described previously. Such geometrical features may include a variety of positive and/or negative features (e.g., projections, holes, notches, and/or the like) that are recognizable by the camera. These geometrical features may facilitate determining the position of the guide probe 1410.

In at least one embodiment, the targeting system 1310 may be configured to track the position/orientation of the guide probe 1410 and update the entry point to a new desired entry point based on the position/orientation of the guide probe 1410. For example, the operator may decide that a planned trajectory entry point is not desirable (e.g., because the current trajectory and/or current entry point of the planned trajectory is located over a wound, a sore, or some other kind of obstruction, such as a bandage, etc.). The operator may wish to relocate the entry point to another location on the patient's skin away from the wound, sore, or obstruction. However, relocating the entry point will require a trajectory update to keep the operator aligned with the target deep inside the patient. Accordingly, in this embodiment, the targeting system 1310 may track the position/orientation of the guide probe 1410 via the optical markers and/or geometrical features. The targeting system 1310 may then receive an indication from the operator that the guide probe 1410 is now pointing at the new desired entry point. The targeting system 1310 may then recalculate the trajectory based on the position of the new desired entry point in order to keep the operator aligned with the target deep inside the patient. The targeting system 1310 may then project the new trajectory through the first and second light sources to help the operator align the guide probe 1410 to the updated trajectory.

In other embodiments, active visualization aids (not shown) are contemplated. For example, guide probes can be made active via the addition of electronic components. This may be advantageous when the intersection of laser light sources may not be directly visualized. In this scenario, the addition of photo-detectors, such as a CCD sensor, to sense the incoming laser light can be used to provide feedback to the operator. The guide probe could alert the operator if the light sensor is not illuminated in a way that lines up with the center line. This feedback may be provided in any manner, including via simple LED lights, via a small LCD display with a "bulls-eye" display to aim the operator in adjustment, etc. Another issue that may potentially arise is when the tool is thick. For example, the screwdriver for pedicle screw insertion can be about 5 mm to 6 mm thick. A guide probe with a hollow middle tube to accommodate this thickness may not be accurate if the lasers converged on the tube surface since the trajectory will be offset by the tool's radius (e.g., about 2.5 mm to 3 mm). In this case, the addition of electronics can help improve accuracy. For example, the visualization guide may have built-in gyroscopes to "lock in" a trajectory. The guide tube can also have a transparent section that allows the operator to line up the centerline accurately with the lasers. Once this occurs, the gyroscope can be used to lock in the trajectory. In this manner, the gyroscope can provide information for small adjustments in trajectory and help the operator stay in alignment. Similarly, in this example feedback can be provided to the operator via LED's, a small LCD display, etc.

Figure 25:
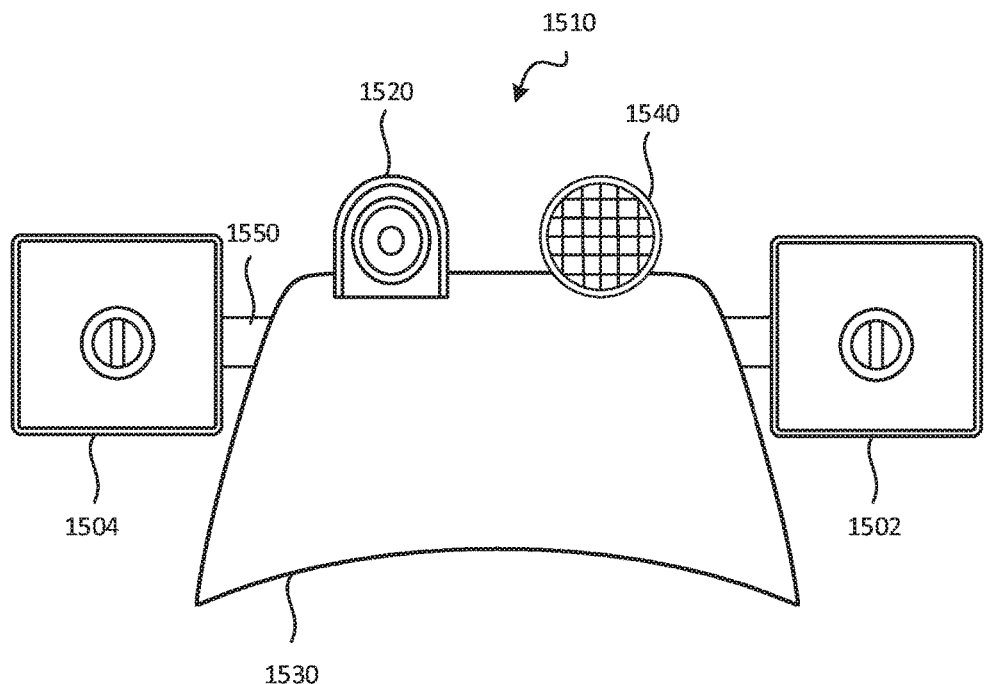
FIG. 25 is a front elevation view of a targeting system including an image-capture device and a structured light device, according to another embodiment of the present disclosure.
Figure 26:
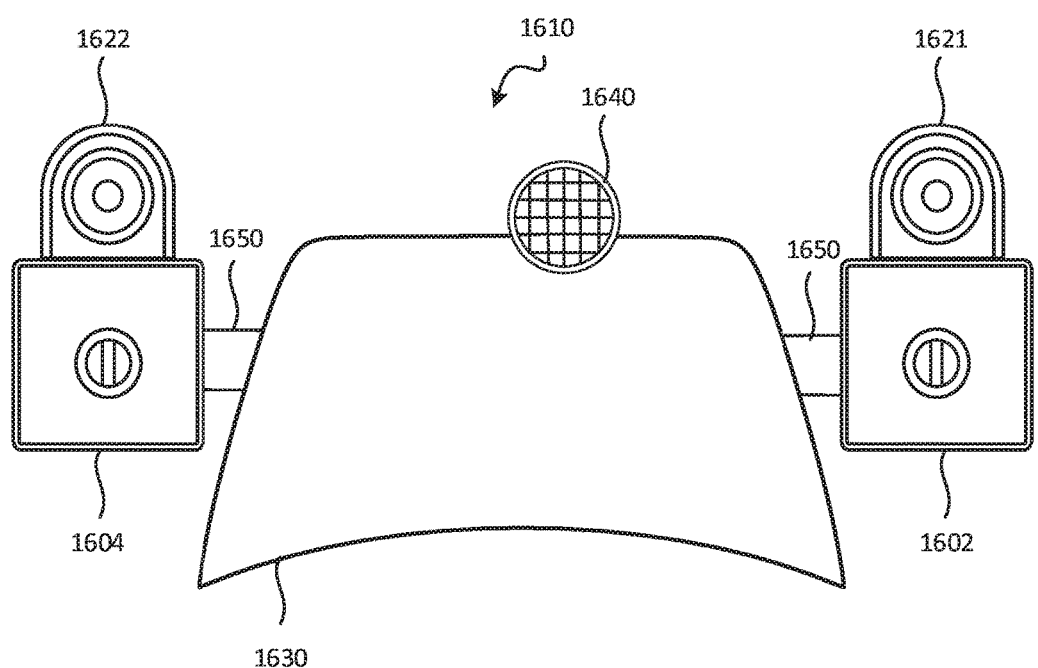
FIG. 26 is a front elevation view of a targeting system including multiple image-capture devices and a structured light device, according to another embodiment of the present disclosure.

FIGS. 25 and 26 illustrate targeting systems 1510, 1610 for providing visualization of a trajectory for a medical instrument, according to alternative embodiments of the present disclosure. The targeting systems 1510, 1610 may be similar to the targeting system 1310 discussed above and may include image capture systems including cameras 1520, 1621, 1622, illumination systems including laser modules 1502, 1504, 1602, 1604, base units 1530, 1630, laser mounting posts 1550, 1650, controllers (not shown), and rotatable armatures (not shown). The targeting systems 1510, 1610 may also include structured light sources 1540, 1640.

The structured light sources 1540, 1640 may be configured to emit structured light patterns to facilitate 3-D mapping of the anatomical features of the patient. An undeformed structured light pattern (e.g., the structured light pattern projected on a flat surface) may be used as calibration data, and the image captured of the patient's anatomy with a deformed structured light pattern can be used to quickly generate a 3-D surface map. This technique has the advantage of speed since few (sometimes even a single) images are needed to map a 3-D surface. FIGS. 27 and 28 illustrate two example structured light patterns that may be emitted by the structured light sources 1540, 1640 shown in FIGS. 25 and 26. These include but are not limited to: FIG. 27 structured light "grid" pattern with predefined grid spacing and orientation and FIG. 28 structured light "dot matrix" pattern with predefined dot density and spacing.

FIG. 29 illustrates how a structured light source associated with a targeting system 1710 may be configured to shine down on the anatomical features of a patient, (e.g., the patient's face), causing the structured light pattern to conform itself to the patient's facial anatomical features. In FIG. 29, the targeting system 1710 is shown attached to the forehead of the patient. However, the targeting systems described herein may also be detached from the patient, as will be shown in FIGS. 32-34. The image capture system of the targeting system 1710 shown in FIG. 29 may capture images of the reflections of structured light patterns that are reflected from the patient's face. Image processing software may then be used to analyze the images and create a 3-D surface map of part of the patient's anatomy. This 3-D map may be combined with other 3-D images to register the patient's actual physical space with pre-operative 3-D images that were taken of the patient (e.g., CT scans, MRI scans, etc.) without the need for pre-scan fiducials.

Figure 30:
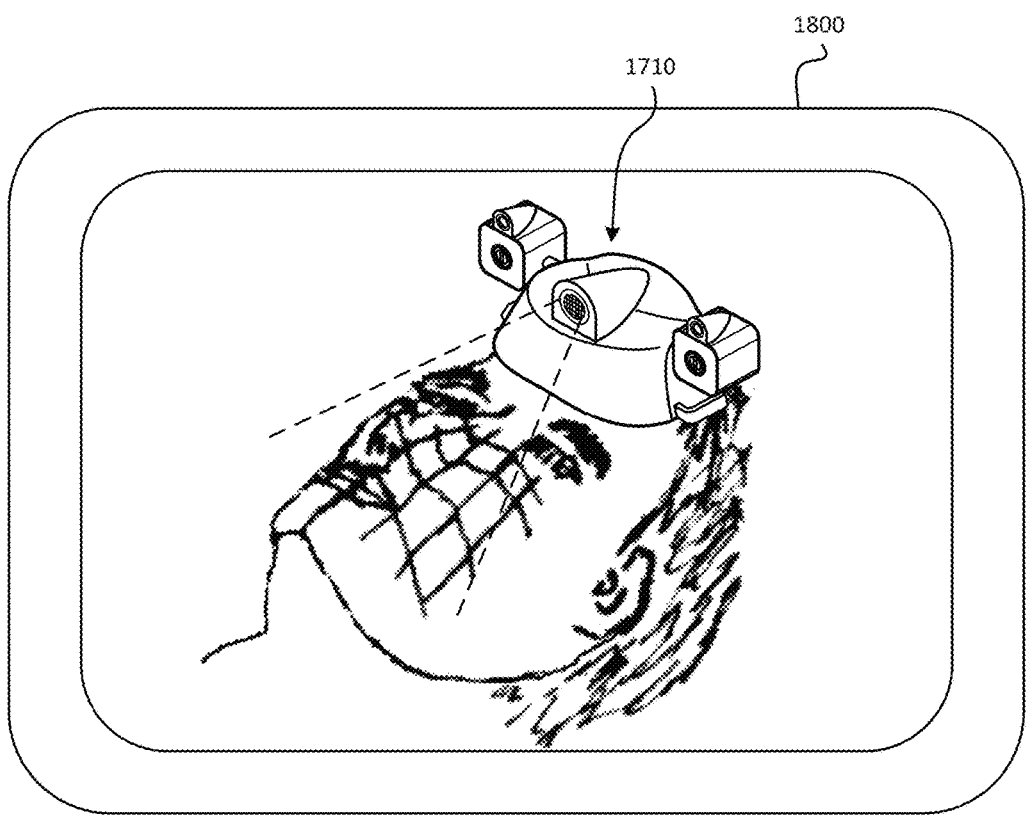
FIG. 30 illustrates a camera/display device such as a smartphone or tablet, displaying the targeting system and patient of FIG. 29.

FIG. 30 illustrates a mobile camera/display device 1800 (which also may be referred to as a screen device 1800) displaying the targeting system 1710 and patient shown in FIG. 29. The screen device 1800 may be any device that includes a camera and a display including, but not limited to: a smart phone, a tablet, a workstation, a computer, a laptop, a PDA, a smart watch, a hand held device, and the like. The device 1800 may also include at least one camera (not shown) which may be located on the back side of the screen device 1800 to enable the user to point the camera toward the patient and take images of the patient while simultaneously viewing a display of the patient on the screen device 1800.

The screen device 1800 may also include software that can interpret the reflections of the structured light that are contained in the images of the patient's face and then create 3-D maps of the patient's facial anatomical surface from these images. The screen device 1800 may also utilize the 3-D maps (either taken from targeting system control unit or generated on its own) for registration with other 3-D images of the patient (e.g., CT/MRI scans) in order to create and display augmented virtual images of the patient with overlays of segmented anatomical features or structures hidden deep inside the patient on to a live video feed. For example, the CT/MRI scans of the patient may be segmented to show the patient's brain ventricle structures. These segmented ventricle structures may then be overlaid on the display relative to the patient's facial skin/outer anatomy in such a manner that these ventricle structures appear at the proper depth and location inside the patient relative to the patient's facial skin/outer anatomy. This helps the operator visualize, target, and plan trajectories for structures inside the patient.

Figure 31:
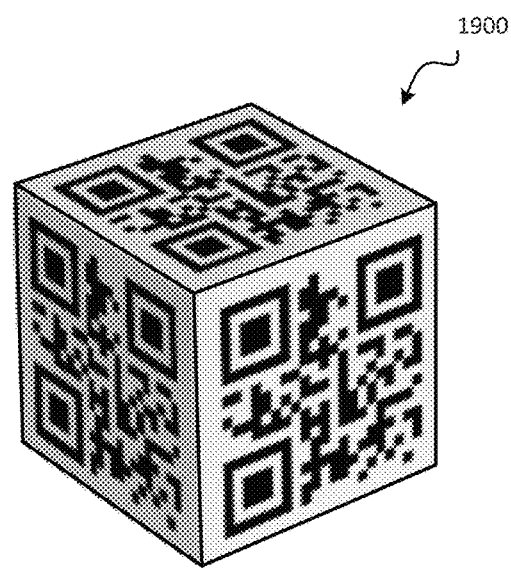
FIG. 31 is a perspective view of a specific embodiment of a patient reference/fiducial marker that can be used by one or more cameras for tracking, containing one or more visible sides of known dimension and high-contrast surface patterns.

FIG. 31 shows an example patient reference/fiducial marker, according to one embodiment of the present disclosure, which may be used with targeting systems disclosed herein. The reference/fiducial marker may be a structure with patterned surfaces of known geometric dimensions with at least one surface visible to the image capture system. The reference/fiducial marker may be a cube 1900, or may have any other shape (planar square, rectangle or triangle, tetrahedral, etc.) with at least one surface visible by the camera system. Such surface(s) may include high contrast patterns. In at least one embodiment, the surfaces of the fiducial marker cube 1900 may include a highly distinctive QR code pattern with unique patterned surfaces which may include alternating designs. A checkerboard pattern would be another possible embodiment of the aforementioned concept (not shown). The patterns may be generally be formed of two high contrast colors, such as black and white, red and green, etc. However, it is understood that any number of colors and patterns are contemplated herein. Moreover, fiducial markers of shapes other than cubes are contemplated, as well as fiducial markers having special reflective coatings, radio opaque materials, and/or any other suitable properties are contemplated herein.

Figure 32:
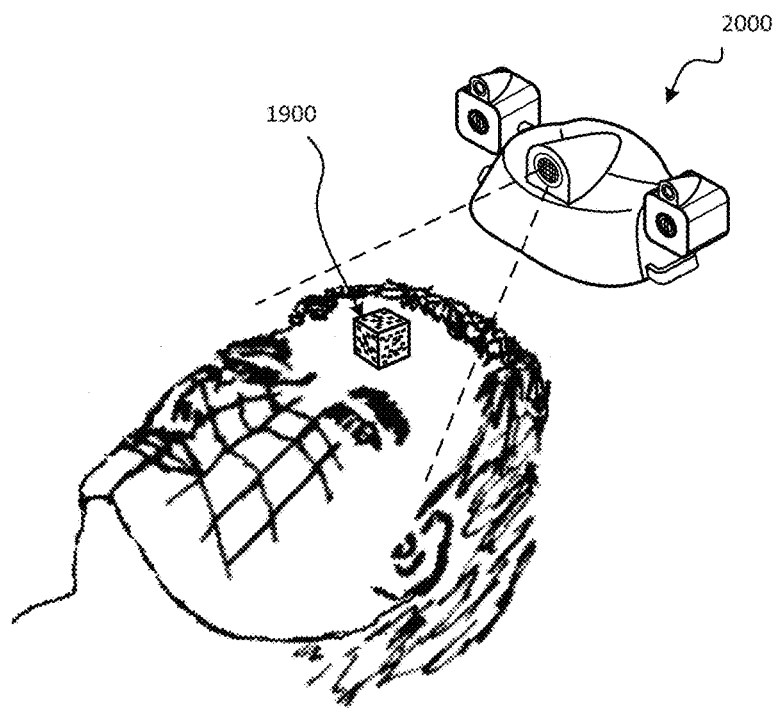
FIG. 32 illustrates a targeting system detached from a patient with the patient reference/fiducial marker of FIG. 31 attached to part of a patient's anatomy for tracking which can be done after the initial medical scan, during or even after the registration step.
Figure 33:
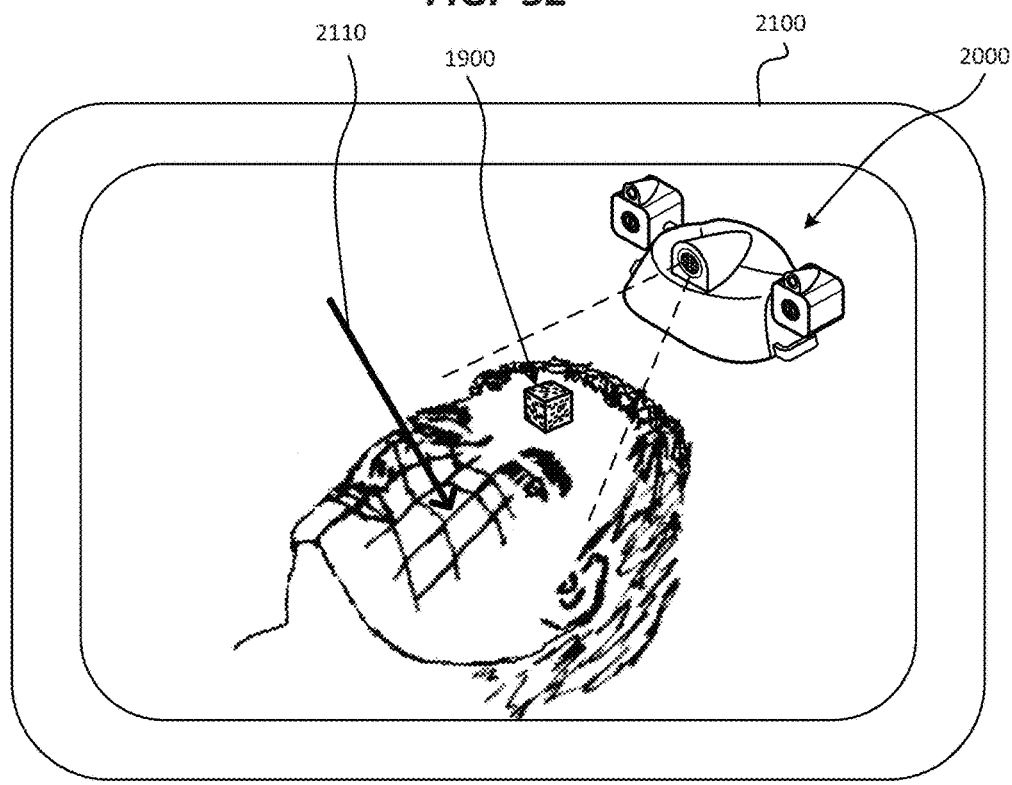
FIG. 33 illustrates a mobile camera/display device displaying the targeting system, patient anatomy, and reference/fiducial marker of FIG. 32 allowing for image overlay of targeting information and planned trajectory onto a live video feed.

FIG. 32 illustrates a targeting system 2000 that is detached from the patient with the reference/fiducial marker 1900 (which may also be referred to as a fiducial marker, cube, or fiducial maker cube) of FIG. 31 coupled to the patient's forehead. The fiducial marker cube 1900 may be used in place of, or in addition to, a structured light pattern reflected from the patient's face in order to track the relative orientation and position of a 3-D map of the patient's anatomy in actual physical space as the patient moves relative to the targeting system 2000 and/or the screen device 2100, as shown in FIG. 33 and discussed in more detail below. The use of a fiducial marker to track the patient's anatomy as it moves around in actual space may be faster than using the structured light pattern to track the patient's movements. This is due to the well-defined nature, high-contrast, and simple geometry of the fiducial marker cube 1900 in this example. Accordingly, in at least one embodiment, a first camera and a second camera may be configured to capture image data of the fiducial marker 1900 and a controller may be configured to receive the image data of the fiducial marker 1900 and continuously update the orientation of a three-dimensional map in space based on a current position of the fiducial marker 1900, and, based on the orientation of the three-dimensional map, determine an updated orientation of a first light source and a second light source to indicate an updated targeting line and an updated trajectory.

Another embodiment of the concept shown in FIG. 32 is to employ the aforementioned reference/fiducial marker for tracking the position of the patient relative to an X-ray unit such as a fluoroscopic C-arm. The targeting system 2000 or its derivative with the camera system and structured light source can be mounted on part of the X-ray system as mentioned before, with the reference/fiducial marker placed on part of the patient's anatomy that can be easily seen by the camera as the X-ray moved from AP to lateral position. To further help with position-locking and calibration of planar X-ray images, the reference/fiducial marker could incorporate radio-opaque material of known geometry (a circle or sphere being the simplest geometry, however other geometries are contemplated) simultaneously with surface patterns. A particular embodiment would be an X-ray opaque sphere placed concentrically inside a cube. The X-ray tube tracked by the camera system can then be reference with the X-ray images of radio-opaque marker to further improve targeting accuracy.

FIG. 33 illustrates a screen device 2100 displaying the targeting system 2000, fiducial maker cube 1900, and patient shown in FIG. 32, including a virtual trajectory 2110, targeting line, or virtual planned trajectory. The screen device 2100 may be similar to the screen device 1800 of FIG. 30 and may include software that can interpret images of the cube to orient the 3-D map of the patient's surface anatomy in actual space as the anatomy part moves around relative to the screen device 2100. The screen device 2100 may also utilize the 3-D map for registration with other 3-D images of the patient (e.g., CT/MRI scans) in order to create and display augmented virtual images of the patient with overlays of planned trajectories and segmented anatomical structures hidden deep inside the patient onto an image or live video stream. This can help the operator visualize, target, and plan trajectories for structures deep inside the patient. FIG. 33 also shows an overlay of a virtual trajectory 2110 targeting a structure (not shown) inside the patient with the entry point of the trajectory on the outer surface of the patient (as can be seen by the tip of the virtual trajectory 2110 touching the face of the patient in FIG. 33). The virtual trajectory 2110 can help the operator visualize where/how to insert the medical instrument during the trajectory planning phase before the procedure begins and/or allow the operator to help monitor the procedure from a remote position while another physician performs the procedure, giving his/her guidance and confirmation to the physician that is performing the procedure.

Figure 34:
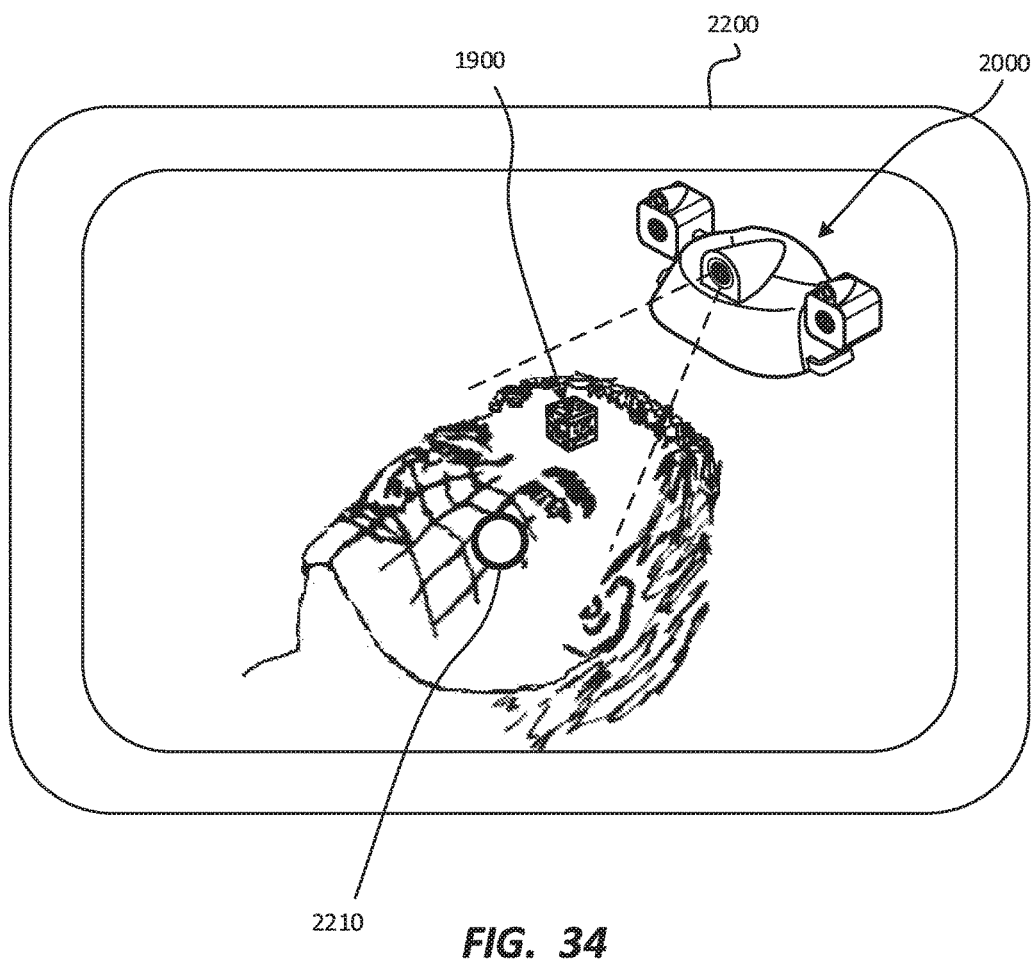
FIG. 34 illustrates a mobile camera/display device displaying the targeting system, patient anatomy, and reference/fiducial marker of FIG. 32 showing a "probe's eye view" of an aligned trajectory via manually positioning of the mobile device.

FIG. 34 illustrates a screen device 2200 displaying the targeting system 2000, patient, and reference/fiducial marker 1900 of FIG. 32 showing a "probe's eye view" of an aligned trajectory over a guide probe 2210. In this embodiment, the operator may take the screen device 2200 and align the screen device 2200 directly over the trajectory such that the screen device 2200 is looking straight down the trajectory to the target inside the patient. This may be referred to as the "probe's eye view" of the trajectory, where the principal axis of the camera is aligned with the planned trajectory and/or the end of the guide probe 2210 (as indicated by the circle in FIG. 34). In the "probe's eye view," the tip and end of the guide probe 2210 line up with the planned trajectory, allowing additional guidance check capabilities. The software of the screen device 2200 may be configured to indicate to the operator when the screen device 2200 is positioned in the "probe's eye view" orientation (e.g., a visual indication may be generated on the display screen and/or a sound may be generated by the screen device 2200 to indicate when the screen device 2200 is positioned in the "probe's eye view" orientation. Once the screen device 2200 is positioned in the "probe's eye view" orientation, the operator may use this information to confirm that the guide probe 2210 is correctly oriented before proceeding with the surgical operation after visual feedback from laser reflections are obtained. This may also enable the operator to help monitor and teach other physicians during training sessions from a remote position.

Figure 35:
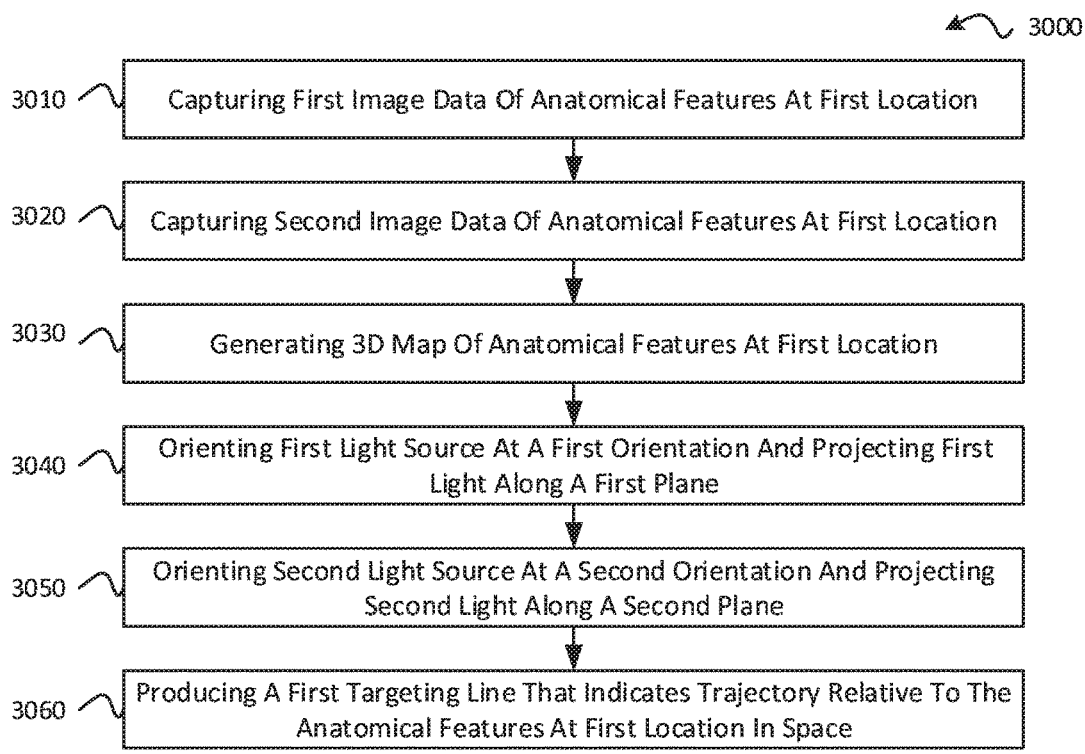
FIG. 35 is a block diagram of a method for providing visualization of a trajectory for a medical instrument, according to one embodiment of the present disclosure.

FIG. 35 is a block diagram of a method 3000 for providing visualization of a trajectory for a medical instrument, according to one embodiment of the present disclosure. The method 3000 may begin at a step 3010 in which first image data of anatomical features of a patient at a first location may be captured, and second image data of anatomical features of the patient at the first location may also be captured in a step 3020 of method 3000. Once the first and second image data have been captured, the method 3000 may then proceed to a step 3030 in which a 3-D map of the anatomical features of the patient at the first location in space may be generated. The 3-D map may then be registered with other image data and/or used to orient a first light source at a first orientation to project first light along a first plane in a step 3040, as well as orient a second light source at a second orientation to project second light along a second plane in a step 3050. The method 3000 may then proceed to a step 3060 in which a first target line is produced that indicates the trajectory relative to the anatomical features of the patient at the first location in space, and the method 3000 may end.

Figure 36:
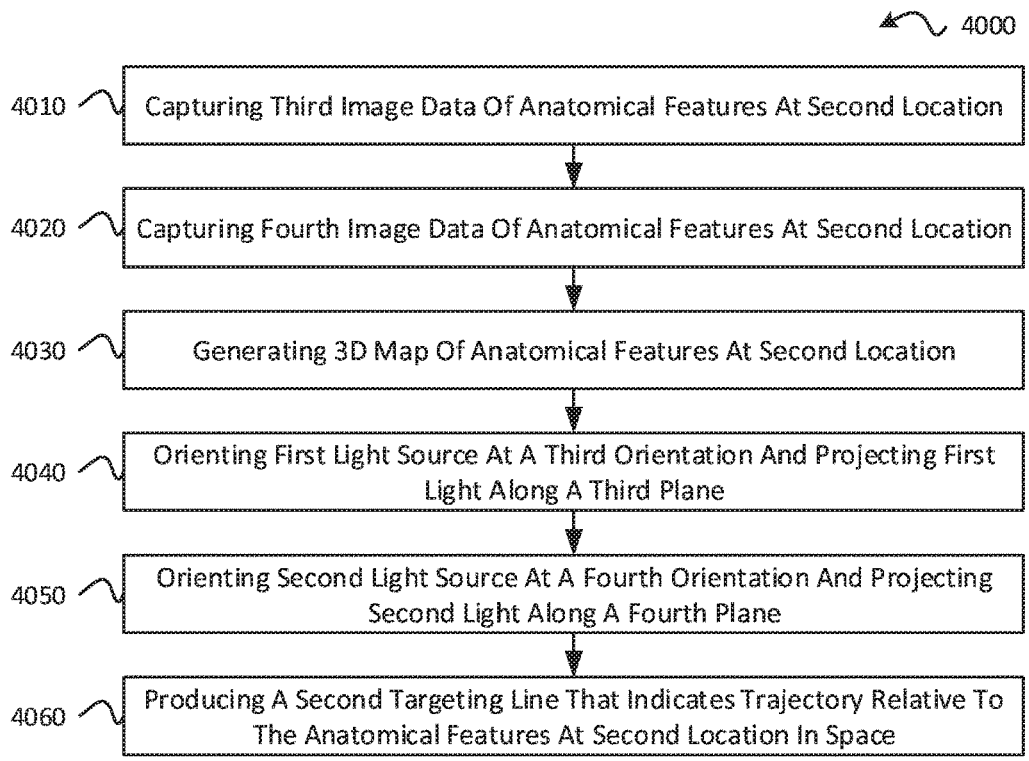
FIG. 36 is a block diagram of a method for providing visualization of an updated trajectory for a medical instrument, according to another embodiment of the present disclosure.

FIG. 36 is a block diagram of a method 4000 for providing visualization of an updated trajectory for a medical instrument, according to another embodiment of the present disclosure. The method 4000 may begin at a step 4010 in which third image data of anatomical features of a patient at a second location may be captured, and fourth image data of anatomical features of the patient at the second location may also be captured in a step 4020 of method 4000. Once the third and fourth image data have been captured, the method 4000 may then proceed to a step 4030 in which a 3-D map of the anatomical features of the patient at the second location in space may be generated. The 3-D map may then be registered with other image data and/or used to orient a first light source at a third orientation to project third light along a third plane in a step 4040, as well as orient a second light source at a fourth orientation to project fourth light along a fourth plane in a step 4050. The method 4000 may then proceed to a step 4060 in which a second target line is produced that indicates the trajectory relative to the anatomical features of the patient at the second location in space, and the method 4000 may end.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

General characteristics of targeting systems according to the present disclosure may include: light weight targeting systems (especially for image guidance system that rest upon a patient's skin or are otherwise attached to a patient); Lightweight materials, such as polymers, composites, lightweight metal alloys, or the like; Electronics miniaturization is also contemplated and on-board electronics may be surface-mounted with small footprints; Lightweight rechargeable batteries may also be used, such as lithium-polymer and/or lithium-ion batteries.

The disclosed technology is intended to be versatile and include a wide range of applications. The aforementioned examples are for illustration purposes only in order to facilitate understanding of concepts. They do not imply that the targeting systems and methods disclosed herein are restricted to only those procedures specifically described herein. Other applications are contemplated and include, but are not limited to, any other medical applications whereby the system may be utilized to target anatomical structures. This includes procedures such as: biopsy of tissues where an entry and target can be specified and the trajectory is planned to avoid critical neurovascular structures; Ablations or electrical stimulation procedures to target an area that cannot be directly visualized (e.g. rhizotomies, neuromodulation procedures, etc.); Joint injections such as knee/hip/shoulder or facet joint injections; Guidance and/or alignment of implants, etc.

For example, alignment of a hip prosthesis can be performed either with pre-operative cross-sectional imaging such as CT scanning or planar imaging taken intra-operatively using fluoroscopy. The system can provide trajectory information for alignment of an acetabular cap and femoral shaft, for example. Similarly, alignment of a knee replacement can be performed whereby the system guides the osteotomy cuts on the tibial or the femoral ends. Appropriate planning can be carried out on cross-sectional imaging pre-operatively or intra-operatively on the fluoroscopy images. Other joint replacement procedures that can benefit from trajectory visualization include ankle, elbow, or shoulder replacements. Artificial intervertebral intervertebral discs can be aligned using the targeting system to maintain anterior-posterior orientation, lateral orientation, and/or true midline position. For spinal fusion procedures, the targeting system can be used to align implants such as contact cages, bone grafts, anterior cervical plates, lateral spinal plates, pedicle screws, pars screws, facet screws, and the like.

The targeting systems and methods disclosed herein can also be used to guide other instruments. Examples include catheter placement procedures, whereby a rigid or semi-rigid catheter is directed at an anatomical target. Planning can be carried out on cross-sectional or planar imaging to define entry points, targets, and safe trajectories.

An external ventricular drain (EVD) for neurosurgical patients is an example of a catheter placement procedure that may benefit from trajectory visualization and planning to avoid injury to critical structures. Port planning for rigid endoscopes is another example of trajectory visualization of surgical instruments. The view through a rigid endoscope can be quite different depending on the placement of the endoscope port and the angle of the shaft. For hip or knee scopes, the ideal view can be planned ahead of time on either cross-sectional or planar imaging. The endoscope trajectory can then be calculated and the entry port marked precisely.

The targeting systems and methods disclosed herein can also be used with ultrasound probes to integrate multiple imaging modalities. This allows the user to take advantage of the most optimal tissue visualization for a given procedure. For example, initial planning can be carried out via bony landmarks on X-ray or CT scans. Once a trajectory is defined, the soft tissue along that trajectory can be further visualized using an ultrasound probe with the probe's central axis directly along the planned trajectory.

The targeting systems and methods disclosed herein can also be used with existing image guidance systems. The laser modules and controller may be mounted in various ways including but not limited to: on the camera of image guidance systems, externally on fixed support structures, directly on the patient, and the like. The controller may interface with image guidance systems. Software integration may allow the image processing terminal (for optical based systems, this is usually a workstation connected to the camera) to be used for planning trajectories and laser position calculations. The data may then be output to the control unit to steer the light sources to their proper positions. In this configuration, the targeting system may augment the functionality of existing image guidance systems while ensuring the surgeon has his or her "eyes on patient" at all times.

Furthermore, the targeting systems and methods disclosed herein can be used with a variety of robot-assisted procedures. This may help the surgeon or surgical team visualize the planned trajectory, especially where a particular step must be performed manually. The manual step can be carried out using the targeting system in addition to the robotic arm's positioning to improve accuracy and speed.

Alternatively, a targeting system as described herein may be mounted on the end of a robotic arm. The robotic arm can be used to position the targeting system in the most optimal position. The rotation of the lasers (for example, roll and yaw) may allow additional degrees of freedom to position the robotic arm such that it will not get in the way of the user while maintaining trajectory visualization accuracy. An example includes robot-assisted hip replacement whereby a trajectory line can be projected before a specific step is carried out (e.g., reaming of the acetabulum). The surgeon can visually confirm the trajectory without the robotic arm blocking the view. The reamer can then be attached to the robotic arm or the surgeon can carry out the reaming process manually with direct visualization of the ideal trajectory. Again, robot-assisted hip replacement is used here to illustrate the general concept, but this concept can be used in any robotic assisted procedures or processes.

The targeting systems and methods disclosed herein can also be used for non-medical applications to provide trajectory visualization. Examples include dental applications such as alignment of implant posts. Pre-operatively taken panoramic X-rays or focused CT scans can be performed and planning may be carried out based on the images obtained from the X-rays or CT scans. Once the trajectories are planned, the targeting system, mounted on an X-ray arm or on the patient, can be used to visualize the trajectories. Other dental procedures include defining root canal trajectories and finding dental fractures.

The targeting systems and methods disclosed herein can be further expanded to industrial applications where certain manufacturing processes cannot be fully automated. In situations where an operator is required to perform a task and where trajectory alignment is critical, the targeting system can be used to provide trajectory visualization. The targeting system can be used with manual procedures such as drilling, welding, finishing and fastening, to align the tool with a predefined trajectory to improve the quality of the finished product.

The claims are not to be interpreted as including means-plus or step-plus-function limitations, unless such a limitation is explicitly recited in a given claim using the phrase(s) "means for" or "step for," respectively. The term "coupled" is defined as connected, although not necessarily directly, and not necessarily mechanically. The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternatives are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

In the foregoing Detailed Description, various features are grouped together in several examples for the purpose of streamlining the disclosure. This method of disclosure is not to be interpreted as reflecting an intention that the disclosure require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Paragraph 6. It will be apparent to those having skill in the art that changes may be made to the details of the above-described embodiments without departing from the underlying principles of the disclosure.

While specific embodiments and applications of the present disclosure have been illustrated and described, it is to be understood that the disclosure is not limited to the precise configuration and components disclosed herein. Various modifications, changes, and variations which will be apparent to those skilled in the art may be made in the arrangement, operation, and details of the methods and systems of the present disclosure disclosed herein without departing from the spirit and scope of the disclosure.

What is claimed is:

1. A targeting system for providing visualization of a trajectory for a medical instrument, the targeting system comprising:
    a base unit;
    an illumination system coupled to the base unit and configured to project light to indicate the trajectory, the illumination system comprising a first light source and a second light source;
    an image capture system coupled to the base unit and configured to capture first image data and second image data of anatomical features of a patient at a first location in space; and
    a controller configured to:
        receive the first image data and the second image data;
        based on the first image data and the second image data, generate a 3-D surface map of the anatomical features of the patient at the first location in space;
        register the 3-D surface map with a pre-operative 3-D image of the anatomical features; and
        based on a registration between the 3-D surface map at the first location in space and the pre-operative 3-D image:
            orient the first light source at a first orientation;
            orient the second light source at a second orientation;
            with the first light source, project first light along a first plane; and
            with the second light source, project second light along a second plane such that, at an intersection of the first plane with the second plane, a targeting line is produced to indicate the trajectory relative to the anatomical features of the patient at the first location in space.

2. The targeting system of claim 1 wherein, the image capture system further comprises:
    a first camera coupled to the base unit and configured to capture first image data of anatomical features of a patient at a first location in space;
    a second camera coupled to the base unit and configured to capture second image data of the anatomical features of the patient at the first location in space, the second camera spaced apart from the first camera by a predetermined distance to form a stereoscopic camera system; and
    the controller is further configured to
        based on the 3-D surface map, determine the first orientation of the first light source and the second orientation of the second light source.

3. The targeting system of claim 2, wherein the first image data and the second image data indicate reflections of ambient light from the anatomical features of the patient.

4. The targeting system of claim 2, wherein:
    the first camera is coupled to the base unit at a known position relative to the first light source and the first image data indicates reflections of the first light from the anatomical features of the patient; and
    the second camera is coupled to the base unit at a known position relative to the second light source and the second image data indicates reflections of the second light from the anatomical features of the patient.

5. The targeting system of claim 2, further comprising a structured light source coupled to the base unit and configured to project a light pattern on the anatomical features of the patient, wherein the first image data and the second image data indicate reflections of the light pattern from the anatomical features of the patient.

6. The targeting system of claim 2, wherein:
the first camera is further configured to capture third image data of the anatomical features of the patient at a second location in space;
the second camera is further configured to capture fourth image data of the anatomical features of the patient at the second location in space; and
the controller is further configured to receive the third image data and the fourth image data and generate a three-dimensional map of the anatomical features of the patient at the second location in space and, based on the three-dimensional map, determine a third orientation of the first light source and a fourth orientation of the second light source at which a second targeting line indicates an updated trajectory.

7. The targeting system of claim 2, further comprising a reference/fiducial marker coupled to the anatomical features of the patient, the reference/fiducial marker comprising a structure with patterned surfaces of known geometric dimensions with at least one surface visible to the image capture system, wherein the first camera and the second camera are configured to capture image data of the reference/fiducial marker and the controller is configured to receive the image data of the reference/fiducial marker and continuously update the orientation of the 3-D surface map in space based on a current position of the reference/fiducial marker, and, based on the orientation of the three-dimensional map, determine an updated orientation of the first light source and the second light source to indicate an updated targeting line and an updated trajectory.

8. The targeting system of claim 2, further comprising a visualization aid configured to be tracked by the image capture system, the visualization aid comprising:
a visualization surface on which the first light and the second light are projected to indicate the trajectory;
at least one of an optical marker and a patterned surface; and
a guide surface positioned such that, with the targeting line projected on the visualization surface, the medical instrument is slidable along the guide surface to move along the trajectory.

9. A method for providing visualization of a trajectory for a medical instrument, the method comprising:
capturing first image data of anatomical features of a patient at a first location in space;
capturing second image data of the anatomical features of the patient at the first location in space;
generating a 3-D surface map of the anatomical features of the patient at the first location in space based on the first and second image data;
registering the 3-D surface map with a pre-operative 3-D image of the anatomical features of the patient; and
based on a registration between the 3-D surface map at the first location in space and the pre-operative 3-D image:
orienting a first light source at a first orientation;
orienting a second light source at a second orientation;
with the first light source, projecting first light along a first plane;
with the second light source, projecting second light along a second plane; and
at an intersection of the first plane with the second plane, producing a targeting line that indicates the trajectory relative to the anatomical features of the patient at the first location in space.

10. The method of claim 9, wherein capturing the first image data and the second image data comprises capturing reflections of ambient light from the anatomical features of the patient.

11. The method of claim 9, wherein capturing the first image data and the second image data comprises capturing reflections of laser light from the anatomical features of the patient.

12. The method of claim 9, wherein capturing the first image data and the second image data comprises capturing reflections of structured light patterns from the anatomical features of the patient.

13. The method of claim 9, further comprising:
capturing third image data of anatomical features of the patient at a second location in space;
capturing fourth image data of the anatomical features of the patient at the second location in space;
generating a second 3-D surface map of the anatomical features of the patient at the second location in space; and
based on the second 3-D surface map of the anatomical features of the patient at the second location in space:
orienting the first light source at a third orientation;
orienting the second light source at a fourth orientation;
with the first light source, projecting the first light along a third plane;
with the second light source, projecting the second light along a fourth plane; and
at an intersection of the third plane with the fourth plane, producing a second targeting line that indicates the trajectory relative to the anatomical features of patient at the second location in space.

14. The method of claim 9, further comprising:
capturing third image data of an object in space relative to the 3-D surface map of the anatomical features of the patient at the first location in space; and
producing an updated targeting line that indicates the trajectory based on the location of the object in space relative to the 3-D surface map of the anatomical features of the patient at the first location in space.

15. The method of claim 14, wherein the object comprises a reference/fiducial marker coupled to the anatomical features of the patient, the reference/fiducial marker comprising a structure with at least one patterned surface.

16. The method of claim 14, wherein the object comprises a visualization aid, the visualization aid comprising:
a visualization surface on which the targeting line is projected;
at least one of an optical marker and a patterned surface; and
a guide surface positioned such that, with the targeting line projected on the visualization surface, the medical instrument is slidable along the guide surface to move along the trajectory.

17. The method of claim 16, further comprising inserting the medical instrument along the trajectory by sliding the medical instrument along a guiding surface of the visualization aid.

18. The method of claim 14, wherein the object comprises a tracing device configured to be tracked by an image capture system to facilitate registration between different image data sets.

19. The method of claim 9, further comprising displaying, on a screen, at least one of a virtual planned trajectory, a current trajectory, a segmented anatomical feature, and the 3-D surface map of the anatomical features of the patient.

20. A targeting system for providing visualization of a trajectory for a medical instrument, the targeting system comprising:
- a base unit;
- a first light source coupled to the base unit, wherein the first light source projects first light along a first plane;
- a second light source coupled to the base unit, wherein the second light source projects second light along a second plane nonparallel to the first plane such that, at an intersection of the first plane with the second plane, the first light and the second light cooperate to produce a first targeting line that indicates the trajectory;
- a camera coupled to the base unit at a known position relative to the first light source and the second light source and configured to capture image data of anatomical features of a patient at a first location in space, the image data indicating reflections of the first light and the second light from the anatomical features of the patient;
- a controller configured to receive the image data and generate a three-dimensional map of the anatomical features of the patient at the first location in space and, based on the three-dimensional map, determine a first orientation of the first light source and a second orientation of the second light source at which the first targeting line indicates the trajectory; and
- a fiducial marker coupled to the anatomical features of the patient, the fiducial marker comprising a cube with patterned surfaces, wherein the camera is configured to capture image data of the fiducial marker and the controller is configured to receive the image data of the fiducial marker and continuously update the orientation of the three-dimensional map in space based on a current position of the fiducial marker, and, based on the orientation of the three-dimensional map, determine an updated orientation of the first light source and the second light source to indicate an updated targeting line and an updated trajectory.

* * * * *